(12) United States Patent
Budhu et al.

(10) Patent No.: US 7,309,721 B2
(45) Date of Patent: *Dec. 18, 2007

(54) AMINOALKYLPHOSPHONATES AND RELATED COMPOUNDS AS EDG RECEPTOR AGONISTS

(75) Inventors: Richard J. Budhu, Dayton, NJ (US); George A. Doherty, Princeton, NJ (US); Jeffrey J. Hale, Westfield, NJ (US); Christopher L. Lynch, Scotch Plains, NJ (US); Sander G. Mills, Scotch Plains, NJ (US); William E. Neway, III, Newton, PA (US)

(73) Assignee: Merck + Co., Inc., Rahway, NJ (US)

( * ) Notice: Subject to any disclaimer, the term of this patent is extended or adjusted under 35 U.S.C. 154(b) by 400 days.

This patent is subject to a terminal disclaimer.

(21) Appl. No.: 10/505,257

(22) PCT Filed: Feb. 27, 2003

(86) PCT No.: PCT/US03/05947

§ 371 (c)(1), (2), (4) Date: Aug. 20, 2004

(87) PCT Pub. No.: WO03/073986

PCT Pub. Date: Sep. 12, 2003

(65) Prior Publication Data

US 2006/0089334 A1    Apr. 27, 2006

Related U.S. Application Data

(60) Provisional application No. 60/360,663, filed on Mar. 1, 2002.

(51) Int. Cl.
| | | |
|---|---|---|
| *A61K 31/185* | (2006.01) | |
| *A61K 31/4196* | (2006.01) | |
| *A61K 31/4192* | (2006.01) | |
| *A61K 31/417* | (2006.01) | |
| *A61K 31/41* | (2006.01) | |
| *C07D 257/04* | (2006.01) | |
| *C07D 233/84* | (2006.01) | |
| *C07D 249/04* | (2006.01) | |
| *C07D 249/12* | (2006.01) | |
| *C07F 9/02* | (2006.01) | |

(52) U.S. Cl. ............ 514/578; 514/382; 514/384; 514/359; 514/398; 548/251; 548/316.4; 548/262.2; 548/263.2; 548/255; 554/1; 554/85; 554/78

(58) Field of Classification Search ........ 514/382, 514/398, 384, 359, 114; 548/255, 262.2, 548/263.2, 316.4; 558/169, 70
See application file for complete search history.

(56) References Cited

U.S. PATENT DOCUMENTS 5,677,282 A    10/1997 Oleksyszyn et al.
5,728,650 A    3/1998 Fisher et al.
5,830,869 A    11/1998 Mitchell et al.
6,437,165 B1 *  8/2002 Mandala et al. ............ 558/169

FOREIGN PATENT DOCUMENTS

| EP | 181833 | 5/1986 |
| EP | 467856 | 1/1992 |
| EP | 778263 | 11/1997 |
| WO | WO 98/40055 | 9/1988 |
| WO | WO96/31124 A1 | 4/1996 |
| WO | WO 97/25315 | 7/1997 |
| WO | WO02/18395 A1 | 3/2002 |

OTHER PUBLICATIONS

Lopez, et al., Tetrahedron, "N-(Diphenylmethylene) glycinate as Anionic Glycine Equivalent. Monoalkylation, Dialkylation and Michael Additions Under Solid-Liquid Phase-Transfer Catalysis", vol. 52, No. 24, pp. 8365-8386, 1996.
Guillena, et al., Tetrahedron, "Stereoselective Synthesis of 2,3-Disubstituted Glutamic Acid Derivatives by Conjugate Addition to 3,4-Didehydropyroglutamates", vol. 54, No. 32, pp. 9447-9456, 1998.
Borea, et al., Farmaco, Ed. Sci., Brain Receptor Binding of Analogues of Y-Aminobutyric Acid (GABA), vol. 38, No. 6, pp. 411-417, 1983.
Yanagisawa, et al., Chemistry Letters, "Synthesis of Statine and Its Analogues", vol. 4, pp. 687-690, 1989.
Guillena, et al., "Synthesis of 2-substituted 4-methyleneglutamic acids and their cyclopropyl analogues", Anales de Quimica Int. ed., vol. 92, pp. 362-369, 1996.
Chemical Abstract, Database Accession No. RN 330645-19-7.
Chemical Abstract, Database Accession No. RN 339345-94-7.
Child, R.G., et al—ARZNEIM—Forsch, vol. 30, No. 1, pp. 695-702, 1980.
Chemical Abstract, Database Accession No. RN333429-89-3.
Chemical Abstract, Database Accession No. RN3833373-17-9.
Chemical Abstract, Database Accession No. RN372144-19-9.

* cited by examiner

*Primary Examiner*—Rebecca Anderson
*Assistant Examiner*—Yong Chu
(74) *Attorney, Agent, or Firm*—William Krovatin; Raynard Yuro

(57) ABSTRACT

The present invention encompasses compounds or Formula (I): as well as the pharmaceutically acceptable salts and hydrates thereof. The compounds are useful for treating immune mediated diseases and conditions, such as bone marrow, organ and tissue transplant rejection. Pharmaceutical compositions and methods of use are included.

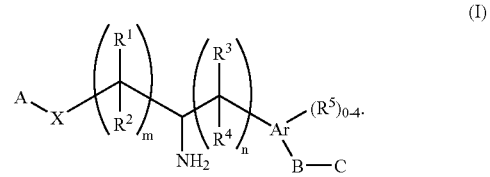

(I)

15 Claims, No Drawings

AMINOALKYLPHOSPHONATES AND RELATED COMPOUNDS AS EDG RECEPTOR AGONISTS

CROSS REFERENCE TO RELATED APPLICATIONS

This application is a U.S. National Phase application under 35 U.S.C. § 371 of PCT Application No. PCT/US03/05947, filed Feb. 27, 2003, which claims priority under 35 U.S.C. 119 to U.S. No. 60/360,663, filed Mar. 1, 2002.

BACKGROUND OF THE INVENTION

The present invention is related to compounds that are $S1P_1$/Edg1 receptor agonists and thus have immunosuppressive activities by producing lymphocyte sequestration in secondary lymphoid tissues. The invention is also directed to pharmaceutical compositions containing such compounds and methods of treatment or prevention.

Immunosuppressive agents have been shown to be useful in a wide variety of autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, autoimmune myositis, Wegener's granulomatosis, ichthyosis, Graves ophthalmopathy, atopic dermatitis and asthma. They have also proved useful as part of chemotherapeutic regimens for the treatment of cancers, lymphomas and leukemias.

Although the underlying pathogenesis of each of these conditions may be quite different, they have in common the appearance of a variety of autoantibodies and/or self-reactive lymphocytes. Such self-reactivity may be due, in part, to a loss of the homeostatic controls under which the normal immune system operates. Similarly, following a bone-marrow or an organ transplantation, the host lymphocytes recognize the foreign tissue antigens and begin to produce both cellular and humoral responses including antibodies, cytokines and cytotoxic lymphocytes which lead to graft rejection.

One end result of an autoimmune or a rejection process is tissue destruction caused by inflammatory cells and the mediators they release. Anti-inflammatory agents such as NSAIDs act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb to infection as they are to their autoimmune disease.

Cyclosporin A is a drug used to prevent rejection of transplanted organs. FK-506 is another drug approved for the prevention of transplant organ rejection, and in particular, liver transplantation. Cyclosporin A and FK-506 act by inhibiting the body's immune system from mobilizing its vast arsenal of natural protecting agents to reject the transplant's foreign protein. Cyclosporin A was approved for the treatment of severe psoriasis and has been approved by European regulatory agencies for the treatment of atopic dermatitis.

Though they are effective in delaying or suppressing transplant rejection, Cyclosporin A and FK-506 are known to cause several undesirable side effects including nephrotoxicity, neurotoxicity, and gastrointestinal discomfort. Therefore, an immunosuppressant without these side effects still remains to be developed and would be highly desirable.

The immunosuppressive compound FTY720 is a lymphocyte sequestration agent currently in clinical trials. FTY720 is metabolized in mammals to a compound that is a potent agonist of sphingosine 1-phosphate receptors. Agonism of sphingosine 1-phosphate receptors induces the sequestration of lymphocytes (T-cells and B-cells) in lymph nodes and Peyer's patches without lymphodepletion. Such immunosuppression is desirable to prevent rejection after organ transplantation and in the treatment of autoimmune disorders.

Sphingosine 1-phosphate is a bioactive sphingolipid metabolite that is secreted by hematopoietic cells and stored and released from activated platelets. Yatomi, Y., T. Ohmori, O. Rile, F. Kazama, H. Okamoto, T. Sano, K. Satoh, S. Kume, G. Tigyi, Y. Igarashi, and Y. Ozaki. 2000. *Blood.* 96:3431-8. It acts as an agonist on a family of G protein-coupled receptors to regulate cell proliferation, differentiation, survival, and motility. Fukushima, N., I. Ishii, J. J. A. Contos, J. A. Weiner, and J. Chun. 2001. Lysophospholipid receptors. Annu. Rev. Pharmacol. Toxicol. 41:507-34; Hla, T., M.-J. Lee, N. Ancellin, J. H. Paik, and M. J. Kluk. 2001. Lysophospholipids—Receptor revelations. *Science.* 294: 1875-1878; Spiegel, S., and S. Milstien. 2000. Functions of a new family of sphingosine-1-phosphate receptors. *Biochim. Biophys. Acta.* 1484:107-16; Pyne, S., and N. Pyne. 2000. Sphingosine 1-phosphate signalling via the endothelial differentiation gene family of G-protein coupled receptors. *Pharm. & Therapeutics.* 88:115-131. Five sphingosine 1-phosphate receptors have been identified ($S1P_1$, $S1P_2$, $S1P_3$, $S1P_4$, and $S1P_5$, also known as endothelial differentiation genes Edg1, Edg5, Edg3, Edg6, Edg8), that have widespread cellular and tissue distribution and are well conserved in human and rodent species (see Table). Binding to S1P receptors elicits signal transduction through Gq-, Gi/o, G12-, G13-, and Rho-dependent pathways. Ligand-induced activation of $S1P_1$ and $S1P_3$ has been shown to promote angiogenesis, chemotaxis, and adherens junction assembly through Rac- and Rho-, see Lee, M.-J., S. Thangada, K. P. Claffey, N. Ancellin, C. H. Liu, M. Kluk, M. Volpi, R. I. Sha'afi, and T. Hla. 1999. *Cell.* 99:301-12, whereas agonism of $S1P_2$ promotes neurite retraction, see Van Brocklyn, J. R., Z. Tu, L. C. Edsall, R. R. Schmidt, and S. Spiegel. 1999. *J. Biol. Chem.* 274:4626-4632, and inhibits chemotaxis by blocking Rac activation, see Okamoto, H., N. Takuwa, T. Yokomizo, N. Sugimoto, S. Sakurada, H. Shigematsu, and Y. Takuwa. 2000. *Mol. Cell. Biol.* 20:9247-9261. $S1P_4$ is localized to hematopoietic cells and tissues, see Graeler, M. H., G. Bernhardt, and M. Lipp. 1999. *Curr. Top. Microbiol. Immunol.* 246:131-6, whereas $S1P_5$ is primarily a neuronal receptor with some expression in lymphoid tissue, see Im, D. S., C. E. Heise, N. Ancellin, B. F. O'Dowd, G. J. Shei, R. P. Heavens, M. R. Rigby, T. Hla, S. Mandala, G. McAllister, S. R. George, and K. R. Lynch. 2000. *J. Biol. Chem.* 275:14281-6. Administration of sphingosine 1-phosphate to animals induces systemic sequestration of peripheral blood lymphocytes into secondary lymphoid organs, stimulates FGF-mediated blood vessel growth and differentiation, see Lee, et al., supra, but also has cardiovascular effects that limit the utility of sphingosine 1-phosphate as a therapeutic agent, see Sugiyama, A., N. N. Aye, Y. Yatomi, Y. Ozaki, and K. Hashimoto. 2000. *Jpn. J. Pharmacol.* 82:338-342. The reduced heart rate and blood pressure measured with sphingosine 1-phosphate is associated with its non-selective, potent agonist activity on all S1P receptors.

The present invention encompasses compounds which are agonists of the S1P₁/Edg1 receptor having selectivity over the S1P3/Edg3 receptor. An S1P₁/Edg1 receptor selective agonist has advantages over current therapies and extends the therapeutic window of lymphocytes sequestration agents, allowing better tolerability with higher dosing and thus improving efficacy as monotherapy.

While the main use for immunosuppressants is in treating bone marrow, organ and transplant rejection, other uses for such compounds include the treatment of arthritis, in particular, rheumatoid arthritis, insulin and non-insulin dependent diabetes, multiple sclerosis, psoriasis, inflammatory bowel disease, Crohn's disease, lupus erythematosis and the like.

Thus, the present invention is focused on providing immunosuppressant compounds that are safer and more effective than prior compounds. These and other objects will be apparent to those of ordinary skill in the art from the description contained herein.

Summary of S1P receptors

| Name | Synonyms | Coupled G proteins | mRNA expression |
|---|---|---|---|
| S1P₁ | Edg1, LP$_{B1}$ | G$_{i/o}$ | Widely distributed, endothelial cells |
| S1P₂ | Edg5, LP$_{B2}$, AGR16, H218 | G$_{i/o}$, G$_q$, G$_{12/13}$ | Widely distributed, vascular smooth muscle cells |
| S1P₃ | Edg3, LP$_{B3}$ | G$_{i/o}$, G$_q$, G$_{12/13}$ | Widely distributed, endothelial cells |
| S1P₄ | Edg6, LP$_{C1}$ | G$_{i/o}$ | Lymphoid tissues, lymphocytic cell lines |
| S1P₅ | Edg8, LP$_{B4}$, NRG1 | G$_{i/o}$ | Brain, spleen |

SUMMARY OF THE INVENTION

The present invention encompasses compounds of Formula I:

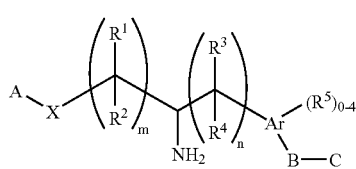

as well as the pharmaceutically acceptable salts and hydrates thereof. The compounds are useful for treating immune mediated diseases and conditions, such as bone marrow, organ and tissue transplant rejection. Pharmaceutical compositions and methods of use are included.

DETAILED DESCRIPTION OF THE INVENTION

The present invention encompasses compounds represented by Formula I:

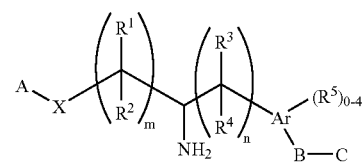

or a pharmaceutically acceptable salt or hydrate thereof, wherein:

Ar is phenyl or naphthyl;
m=1, 2, 3, or 4;
n=0, 1, 2, 3, or 4;
X is a bond, O, NH or S(O)$_k$, wherein k is 0, 1 or 2;
A is selected from the group consisting of: —CO₂H, —PO₃H₂, —PO₂H₂, —SO₃H, —PO(R⁸)OH,

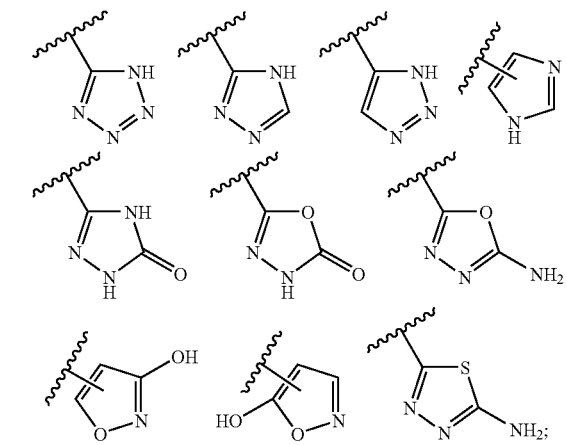

each R¹ is independently selected from the group consisting of: hydrogen, halo, hydroxy, —CO₂H, C$_{1-4}$alkyl, C$_{1-4}$alkoxy, C$_{1-4}$alkylthio and aryl, wherein said C$_{1-4}$alkyl, C$_{1-4}$alkoxy and C$_{1-4}$alkylthio are each optionally substituted from one up to the maximum number of substitutable positions with halo and wherein said aryl is optionally substituted with 1-5 substituents independently selected from halo and C$_{1-4}$alkyl, or when m is 2, 3, or 4, two R¹ groups on adjacent carbon atoms may be joined together to form a double bond;

each R³ is independently selected from the group consisting of: hydrogen, halo, hydroxy, —CO₂H, C$_{1-4}$alkyl, C$_{1-4}$alkoxy, C$_{1-4}$alkylthio and aryl, wherein said C$_{1-4}$alkyl, C$_{1-4}$alkoxy and C$_{1-4}$alkylthio are each optionally substituted from one up to the maximum number of substitutable positions with halo and wherein said aryl is optionally substituted with 1-5 substituents independently selected from halo and C$_{1-4}$alkyl, or when n is 2, 3, or 4, two R³ groups on adjacent carbon atoms may be joined together to form a double bond;

R² and R⁴ are each independently selected from the group consisting of: hydrogen, halo, hydroxy, —CO₂H, C$_{1-4}$alkyl, C$_{1-4}$alkoxy, C$_{1-4}$alkylthio and aryl, wherein said $C_{1-4}$alkyl, $C_{1-4}$alkoxy and $C_{1-4}$alkylthio are each optionally substituted from one up to the maximum number of substitutable positions with halo and wherein said aryl is optionally substituted with 1-5 substituents independently selected from halo and $C_{1-4}$alkyl;

or $R^1$ and $R^2$ or $R^3$ and $R^4$ residing on the same carbon atom may optionally be joined together to form a carbonyl group, each $R^5$ is independently selected from the group consisting of: halo, aryl, $C_{1-6}$alkyl, $C_{3-6}$cycloalkyl, $C_{1-6}$alkoxy, $C_{1-6}$alkylthio and $C_{3-6}$cycloalkoxy, said $C_{1-6}$alkyl, $C_{3-6}$cycloalkyl, $C_{1-6}$alkoxy, $C_{1-6}$alkylthio and $C_{3-6}$cycloalkoxy optionally substituted from one up to the maximum number of substitutable positions with halo, $R^8$ is selected from the group consisting of: $C_{1-4}$alkyl and aryl, wherein said $C_{1-4}$alkyl is optionally substituted with 1-3 halo groups and aryl is optionally substituted with 1-5 substituents independently selected from the group consisting of: halo, $C_{1-6}$alkyl, $C_{3-6}$cycloalkyl, $C_{1-6}$alkoxy, $C_{1-4}$alkylthio and $C_{3-6}$cycloalkoxy, said $C_{1-6}$alkyl, $C_{3-6}$cycloalkyl, $C_{1-6}$alkoxy, $C_{1-4}$alkylthio and $C_{3-6}$cycloalkoxy optionally substituted from one up to the maximum number of substitutable positions with halo, C is selected from the group consisting of:
(1) $C_{1-8}$alkyl, $C_{1-8}$alkoxy, —(C=O)—$C_{1-6}$alkyl or —CHOH—$C_{1-6}$alkyl, said $C_{1-8}$alkyl, $C_{1-8}$alkoxy, —(C=O)—$C_{1-6}$alkyl and —CHOH—$C_{1-6}$alkyl optionally substituted with phenyl, and
(2) phenyl or HET, each optionally substituted from one up to the maximum number of substituable positions with a substituent independently selected from the group consisting of: halo, phenyl, $C_{1-4}$alkyl, $C_{1-4}$alkoxy and aralkyl, said $C_{1-4}$alkyl and $C_{1-4}$alkoxy groups optionally substituted from one up to the maximum number of substitutable positions with a substituent independently selected from halo and hydroxy, and said phenyl and the aryl portion of aralkyl optionally substituted with 1 to 5 groups independently selected from the group consisting of: halo, $C_{1-4}$alkyl and $C_{1-4}$alkoxy, said $C_{1-4}$alkyl and $C_{1-4}$alkoxy optionally substituted with 1-3 halo groups, or C is not present;

when C is not present then B is selected from the group consisting of: phenyl, $C_{5-16}$alkyl, $C_{5-16}$alkenyl, $C_{5-16}$alkynyl, —CHOH—$C_{4-15}$alkyl, —CHOH—$C_{4-15}$alkenyl, —CHOH—$C_{4-15}$alkynyl, $C_{4-15}$alkoxy, —O—$C_{4-15}$alkenyl, —O—$C_{4-15}$alkynyl, $C_{4-15}$alkylthio, —S—$C_{4-15}$alkenyl, —S—$C_{4-15}$alkynyl, —CH$_2$—$C_{3-14}$alkoxy, —CH$_2$—O—$C_{3-14}$alkenyl, —CH$_2$—O—$C_{3-14}$alkynyl, —(C=O)—$C_{4-15}$alkyl, —(C=O)—$C_{4-15}$alkenyl, —(C=O)—$C_{4-15}$alkynyl, —(C=O)—O—$C_{3-14}$alkyl, —(C=O)—O—$C_{3-14}$alkenyl, —(C=O)—O—$C_{3-14}$alkynyl, —(C=O)—N($R^6$)($R^7$)—$C_{3-14}$alkyl, —(C=O)—N($R^6$)($R^7$)—$C_{3-14}$alkenyl, —(C=O)—N($R^6$)($R^7$)—$C_{3-14}$alkynyl, —N($R^6$)($R^7$)—(C=O)—$C_{3-14}$alkyl, —N($R^6$)($R^7$)—(C=O)—$C_{3-14}$alkenyl and —N($R^6$)($R^7$)—(C=O)—$C_{3-14}$alkynyl, when C is phenyl or HET then B is selected from the group consisting of: $C_{1-6}$alkyl, $C_{1-5}$alkoxy, —(C=O)—$C_{1-5}$alkyl, —(C=O)—O—$C_{1-4}$alkyl, —(C=O)—N($R^6$)($R^7$)—$C_{1-4}$alkyl, —(C=O)—, —(CHOH)—, phenyl and HET, said phenyl and HET each optionally substituted from one up to the maximum number of substituable positions with a substituent independently selected from the group consisting of: halo, phenyl, $C_{1-4}$alkyl, $C_{1-4}$alkoxy and aralkyl, said $C_{1-4}$alkyl and $C_{1-4}$alkoxy groups optionally substituted from one up to the maximum number of substitutable positions with a substituent independently selected from halo and hydroxy, and said phenyl and the aryl portion of aralkyl optionally substituted with 1 to 5 groups independently selected from the group consisting of: halo, $C_{1-4}$alkyl and $C_{1-4}$alkoxy, said $C_{1-4}$alkyl and $C_{1-4}$alkoxy optionally substituted with 1-3 halo groups, and when C is $C_{1-8}$alkyl, $C_{1-8}$alkoxy, —(C=O)—$C_{1-6}$alkyl or —CHOH—$C_{1-6}$alkyl then B is phenyl or HET, said phenyl and HET each optionally substituted from one up to the maximum number of substituable positions with a substituent independently selected from the group consisting of: halo, phenyl, $C_{1-4}$alkyl, $C_{1-4}$alkoxy and aralkyl, said $C_{1-4}$alkyl and $C_{1-4}$alkoxy groups optionally substituted from one up to the maximum number of substitutable positions with a substituent independently selected from halo and hydroxy, and said phenyl and the aryl portion of aralkyl optionally substituted with 1 to 5 groups independently selected from the group consisting of: halo, $C_{1-4}$alkyl and $C_{1-4}$alkoxy, said $C_{1-4}$alkyl and $C_{1-4}$alkoxy optionally substituted with 1-3 halo groups; and $R^6$ and $R^7$ are independently selected from the group consisting of: hydrogen, $C_{1-9}$alkyl and —(CH$_2$)$_q$-phenyl, wherein q is 1 to 5 and phenyl is optionally substituted with 1-5 substituents independently selected from the group consisting of: $C_{1-3}$alkyl and $C_{1-3}$alkoxy, each optionally substituted with 1-3 halo groups.

An embodiment of the invention encompasses a compound of Formula I wherein: Ar is phenyl and the group —B—C is attached to the phenyl ring at the 3- or 4-position.

An embodiment of the invention encompasses a compound of Formula I wherein X is a bond, m is 2 and n is 2.

An embodiment of the invention encompasses a compound of Formula I wherein X is selected from O, NH or S, m is 1 and n is 2.

An embodiment of the invention encompasses a compound of Formula I wherein BET is selected from the group consisting of:

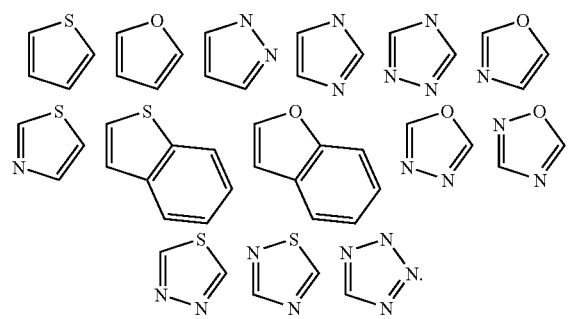

An embodiment of the invention encompasses a compound of Formula I wherein C is not present and B is selected from the group consisting of: $C_{5-16}$alkyl, $C_{5-16}$alkenyl, $C_{5-16}$alkynyl, —CHOH—$C_{4-15}$alkyl, —CHOH—$C_{4-15}$alkenyl, —CHOH—$C_{4-15}$alkynyl, $C_{4-15}$alkoxy, —O—$C_{4-15}$ alkenyl, —O—$C_{4-15}$alkynyl, $C_{4-15}$alkylthio, —S—$C_{4-15}$ alkenyl, —S—$C_{4-15}$alkynyl, —CH$_2$—$C_{3-14}$alkoxy, —CH$_2$—O—$C_{3-14}$alkenyl, —CH$_2$—O—$C_{3-14}$ alkynyl, —(C=O)—$C_{4-15}$alkyl, —(C=O)—$C_{4-15}$alkenyl, —(C=O)—$C_{4-15}$alkynyl, —(C=O)—O—$C_{3-14}$alkyl, —(C=O)—O—$C_{3-14}$alkenyl, —(C=O)—O—$C_{3-14}$alkynyl, —(C=O)—N($R^6$)($R^7$)—$C_{3-14}$alkyl, —(C=O)—N($R^6$)($R^7$)—$C_{3-14}$alkenyl, —(C=O)—N($R^6$)($R^7$)—$C_{3-14}$alkynyl, —N(R⁶)(R⁷)—(C=O)—C₃₋₁₄alkyl, —N(R⁶)(R⁷)—(C=O)-C₃₋₁₄alkenyl and —N(R⁶)(R⁷)—(C=O)—C₃₋₁₄alkynyl.

An embodiment of the invention encompasses a compound of Formula I wherein C is phenyl and B is selected from the group consisting of: C₁₋₆alkyl, C₁₋₅alkoxy, —(C=O)—C₁₋₅alkyl, —(C=O)—O—C₁₋₄alkyl and —(C=O)—N(R⁶)(R⁷)—C₁₋₄alkyl.

An embodiment of the invention encompasses a compound of Formula I wherein:

B—C is selected from the group consisting of:
(1) B is C₇₋₁₀alkyl and C is not present,
(2) B is C₆₋₉alkoxy and C is not present,
(3) B is C₁₋₆alkyl or C₁₋₅alkoxy and C is phenyl, or
(4) B—C is

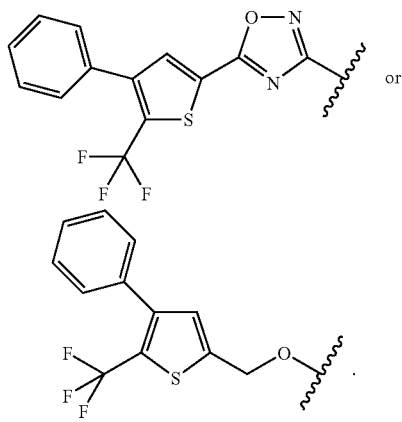

An embodiment of the invention encompasses a compound of Formula I wherein:
when X is a bond then m is 2 and n is 2,
when X is O, NH or S then m is 1 and n is 2,
Ar is phenyl and
the group —B—C is attached to the phenyl ring at the 3- or 4-position.

Within this embodiment embodiment is encompassed a compound of Formula I wherein C is not present and B is selected from the group consisting of: C₅₋₁₆alkyl, C₅₋₁₆alkenyl, C₅₋₁₆alkynyl, —CHOH—C₄₋₁₅alkyl, —CHOH—C₄₋₁₅ alkenyl, —CHOH—C₄₋₁₅alkynyl, C₄₋₁₅alkoxy, —O—C₄₋₁₅ alkenyl, —O—C₄₋₁₅alkynyl, C₄₋₁₅alkylthio, —S—C₄₋₁₅ alkenyl, —S—C₄₋₁₅alkynyl, —CH₂—C₃₋₁₄alkoxy, —CH₂—O—C₃₋₁₄alkenyl, —CH₂—O—C₃₋₁₄ alkynyl, —(C=O)—C₄₋₁₅alkyl, —(C=O)-C₄₋₁₅alkenyl, —(C=O)-C₄₋₁₅alkynyl, —(C=O)—O—C₃₋₁₄alkyl, —(C=O)—O—C₃₋₁₄alkenyl, —(C=O)—O—C₃₋₁₄alkynyl, —(C=O)—N(R⁶)(R⁷)—C₃₋₁₄alkyl, —(C=O)—N(R⁶)(R⁷)—C₃₋₁₄ alkenyl, —(C=O)—N(R⁶)(R⁷)—C₃₋₁₄alkynyl, —N(R⁶)(R⁷)—(C=O)—C₃₋₁₄alkyl, —N(R6)(R⁷)—(C=O)—C₃₋₁₄ alkenyl and —N(R⁶)(R⁷)—(C=O)—C₃₋₁₄alkynyl.

Further within the embodiment of the invention is encompassed a compound of Formula I wherein C is not present and B is C₇₋₁₀alkyl.

Further within the embodiment of the invention is encompassed wherein C is not present and B is C₆₋₉alkoxy.

Also within this embodiment embodiment is encompassed a compound of Formula I wherein C is phenyl and B is C₃₋₆alkyl.

Also within this embodiment embodiment is encompassed a compound of Formula I wherein A is selected from the group consisting of: —CO₂H, —PO₃H₂, —PO₂H₂, —SO₃H and —PO(R⁸)OH.

For purposes of this specification, when the group —B—C is attached to the phenyl ring at the 3- or 4-position, it means the positions shown in the following:

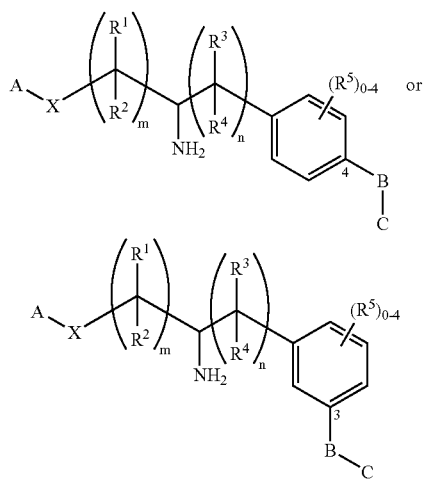

For purposes of this specification, C may be substituted at any substitutable position on B. For example, when B is methoxy and C is thiophene, thiophene replaces a hydrogen on the methoxy group. Further variations are illustrated in the examples that follow. Also, the point of any attachments shown for B is to the Ar group. For example, when B is —(C=O)—C₆₋₁₁ alkynyl this means B is attached to Ar as follows: Ar—(C=O)—C₆₋₁₁alkynyl. C may then be substituted at any substituable position on B.

An embodiment of the invention encompasses a method of treating an immunoregulatory abnormality in a mammalian patient in need of such treatment comprising administering to said patient a compound of Formula I in an amount that is effective for treating said immunoregulatory abnormality.

Within this embodiment is encompassed the above method wherein the immunoregulatory abnormality is an autoimmune or chronic inflammatory disease selected from the group consisting of: systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

Also within this embodiment is encompassed the above method wherein wherein the immunoregulatory abnormality is bone marrow or organ transplant rejection or graft-versus-host disease.

Also within this embodiment is encompassed the above method wherein wherein the immunoregulatory abnormality is selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Also within this embodiment is encompassed the above method wherein wherein the immunoregulatory abnormality is multiple sclerosis Also within this embodiment is encompassed the above method wherein the immunoregulatory abnormality is rheumatoid arthritis Also within this embodiment is encompassed the above method wherein the immunoregulatory abnormality is systemic lupus erythematosus Also within this embodiment is encompassed the above method wherein the immunoregulatory abnormality is psoriasis Also within this embodiment is encompassed the above method wherein the immunoregulatory abnormality is rejection of transplanted organ or tissue Also within this embodiment is encompassed the above method wherein the immunoregulatory abnormality is inflammatory bowel disease.

Also within this embodiment is encompassed the above method wherein the immunoregulatory abnormality is a malignancy of lymphoid origin.

Also within this embodiment is encompassed the above method wherein the immunoregulatory abnormality is acute and chronic lymphocytic leukemias and lymphomas.

Another embodiment of the invention encompasses a method of suppressing the immune system in a mammalian patient in need of immunosuppression comprising administering to said patient an immunosuppressing effective amount of a compound of Formula I.

The invention also encompasses a pharmaceutical composition comprised of a compound of Formula I in combination with a pharmaceutically acceptable carrier.

The compound of Formula II is defined as follows:

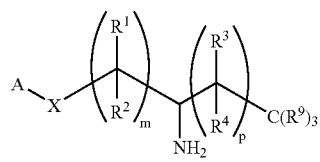

or a pharmaceutically acceptable salt or hydrate thereof, wherein:

m=1, 2, 3, or 4;

p=9 to 20;

X is a bond, O, NH, $S(O)_k$, wherein k is 0, 1 or 2;

A is selected from the group consisting of: $-CO_2H$, $-PO_3H_2$, $-PO_2H_2$, $-SO_3H$, $-PO(R^8)OH$,

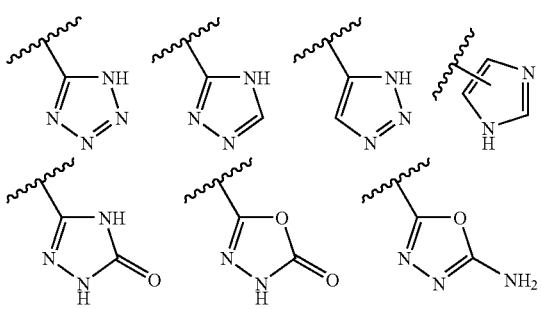

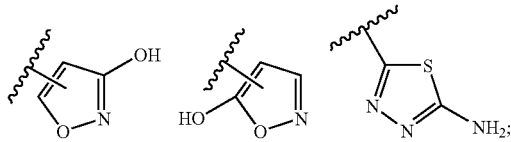

each R¹ is independently selected from the group consisting of: hydrogen, halo, hydroxy, —CO$_2$H, $C_{1-4}$alkyl, $C_{1-4}$alkoxy, $C_{1-4}$alkylthio and aryl, wherein said $C_{1-4}$alkyl, $C_{1-4}$alkoxy and $C_{1-4}$alkylthio are each optionally substituted from one up to the maximum number of substitutable positions with halo and wherein said aryl is optionally substituted with 1-5 substituents independently selected from halo and $C_{1-4}$alkyl, or when m is 2, 3, or 4, two R¹ groups on adjacent carbon atoms may be joined together to form a double bond; each R³ is independently selected from the group consisting of: hydrogen, halo, hydroxy, —CO$_2$H, $C_{1-4}$alkyl, $C_{1-4}$alkoxy, $C_{1-4}$alkylthio and aryl, wherein said $C_{1-4}$alkyl, $C_{1-4}$alkoxy and $C_{1-4}$alkylthio are each optionally substituted from one up to the maximum number of substitutable positions with halo and wherein said aryl is optionally substituted with 1-5 substituents independently selected from halo and $C_{1-4}$alkyl, or when n is 2, 3, or 4, two R³ groups on adjacent carbon atoms may be joined together to form a double bond; and R² and R⁴ are each independently selected from the group consisting of: hydrogen, halo, hydroxy, —CO$_2$H, $C_{1-4}$alkyl, $C_{1-4}$alkoxy, $C_{1-4}$alkylthio and aryl, wherein said $C_{1-4}$alkyl, $C_{1-4}$alkoxy and $C_{1-4}$alkylthio are each optionally substituted from one up to the maximum number of substitutable positions with halo and wherein said aryl is optionally substituted with 1-5 substituents independently selected from halo and $C_{1-4}$alkyl;

or R¹ and R² or R³ and R⁴ residing on the same carbon atom may optionally be joined together to form a carbonyl group, R⁸ is selected from the group consisting of: $C_{1-4}$alkyl and aryl, wherein said $C_{1-4}$alkyl is optionally substituted with 1-3 halo groups and aryl is optionally substituted with 1-3 substituents independently selected from the group consisting of: halo, $C_{1-6}$alkyl, $C_{3-6}$cycloalkyl, $C_{1-6}$alkoxy, $C_{1-6}$alkylthio and $C_{3-6}$cycloalkoxy, said $C_{1-6}$alkyl, $C_{3-6}$cycloalkyl, $C_{1-6}$alkoxy, $C_{1-6}$alkylthio and $C_{3-6}$cycloalkoxy optionally substituted from one up to the maximum number of substitutable positions with halo, R⁹ is selected from the group consisting of: hydrogen, halo, hydroxy, $C_{1-4}$alkoxy, $C_{1-4}$alkylthio and $C_{3-7}$cycloalkyl, wherein said $C_{1-4}$alkoxy, $C_{1-4}$alkylthio and $C_{3-7}$cycloalkyl are each independently optionally substituted from one up to the maximum number of substitutable positions with halo and wherein said aryl is optionally substituted with 1-3 substituents independently selected from halo and $C_{1-4}$alkyl.

Exemplifying the invention are the following compounds:

| Example Number(s) | Structure |
|---|---|
| 1 | 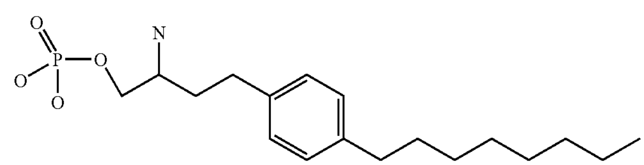 |
| 2 | 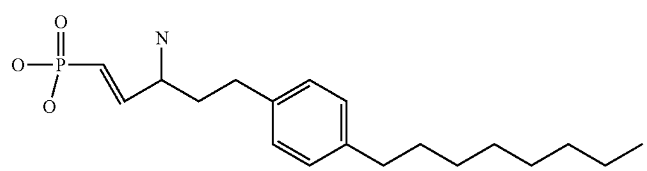 |
| 3 | 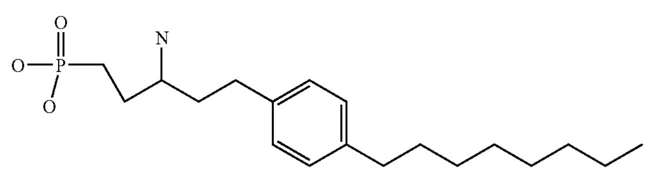 |
| 4 | 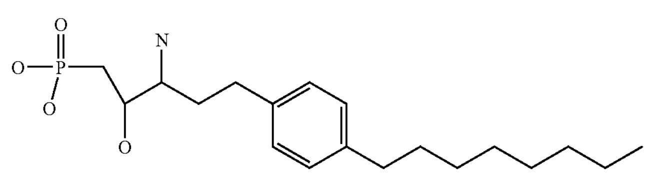 |

-continued

Exemplifying the invention are the following compounds:

| Example Number(s) | Structure |
|---|---|
| 5 | 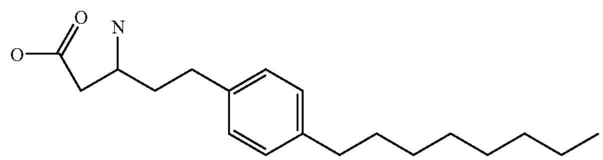 |
| 6 | 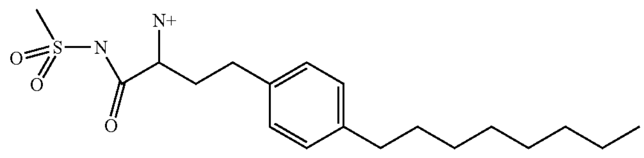 |
| 7 | 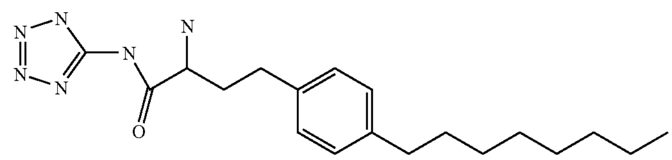 |
| 8 | 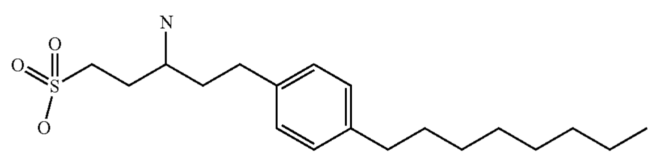 |
| 9 | 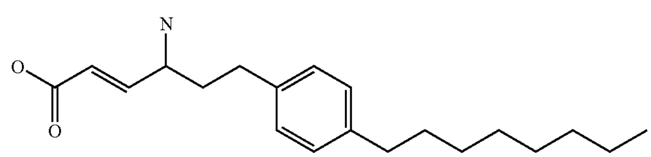 |
| 10 | 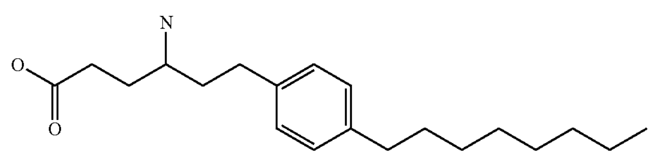 |
| 11 | 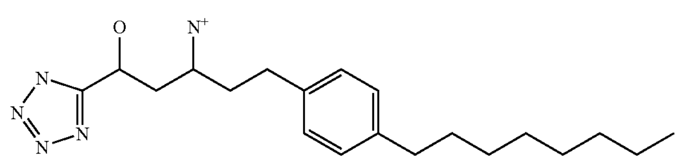 |
| 12-15 | 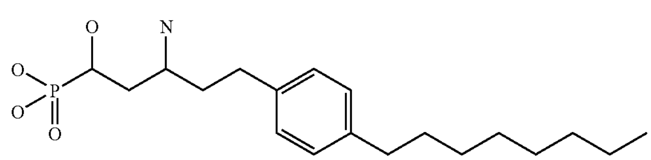 |
| 16 | 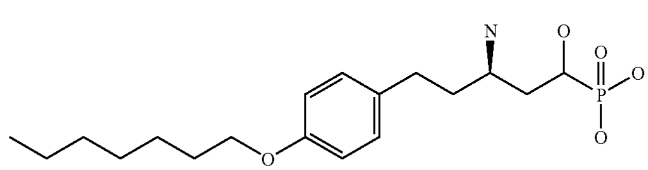 |

-continued
Exemplifying the invention are the following compounds:
| Example Number(s) | Structure |
|---|---|
| 17 | 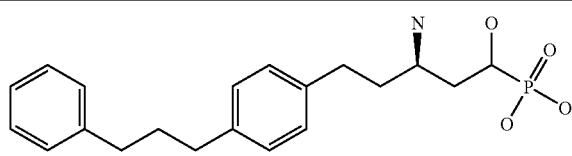 |
| 18 | 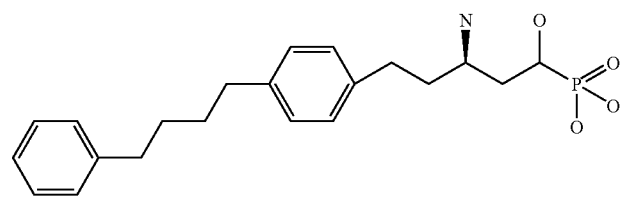 |
| 19 | 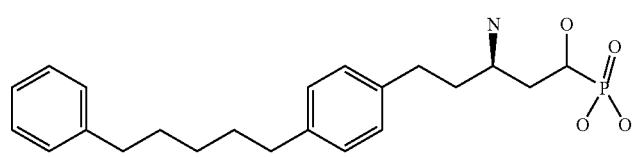 |
| 20 | 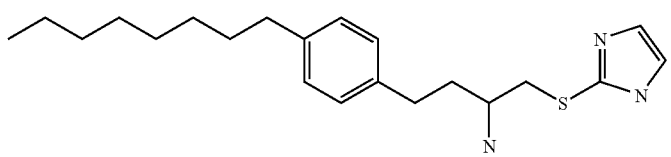 |
| 21 | 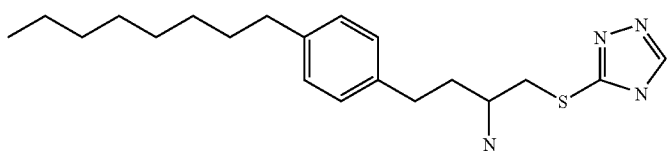 |
| 22 | 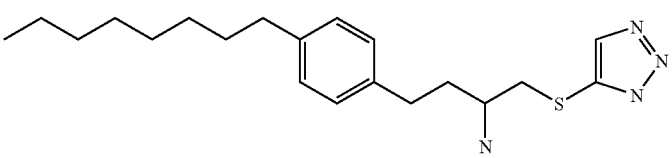 |
| 23 | 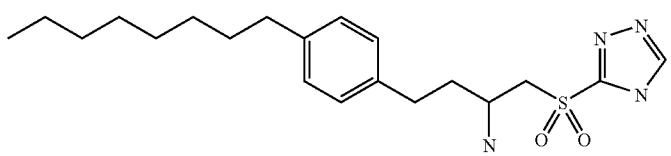 |
| 24 | 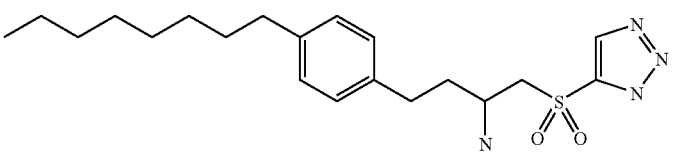 |
| 25 | 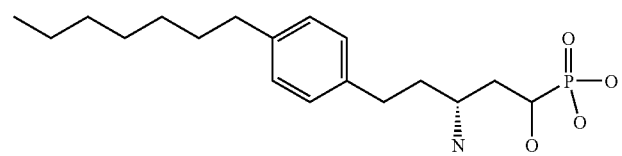 |

-continued
Exemplifying the invention are the following compounds:
| Example Number(s) | Structure |
|---|---|
| 26 | 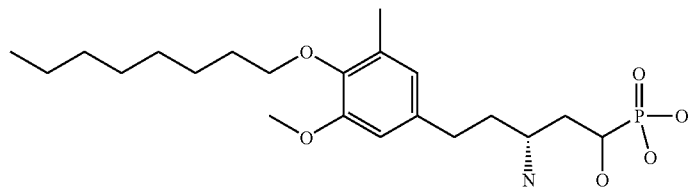 |
| 27 | 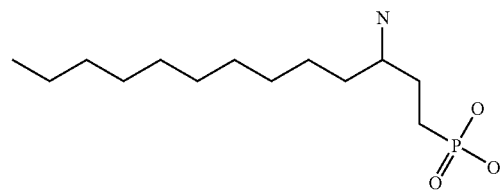 |
| 28 | 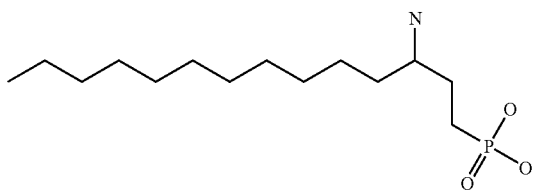 |
| 29 | 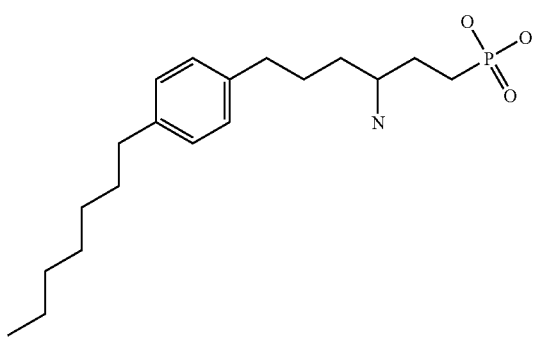 |
| 30 | 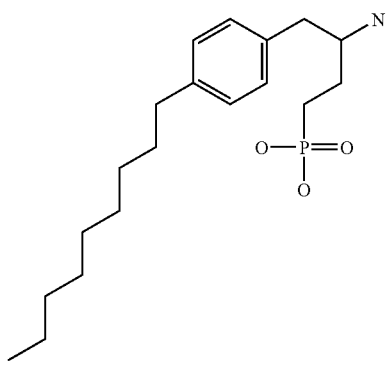 |

-continued
Exemplifying the invention are the following compounds:
| Example Number(s) | Structure |
|---|---|
| 31 | 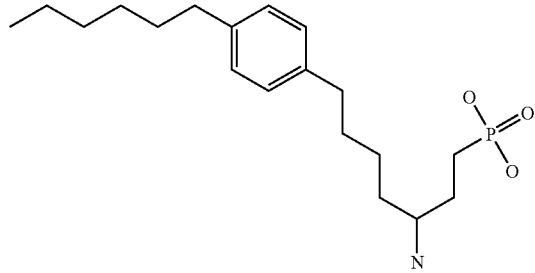 |
| 32 | 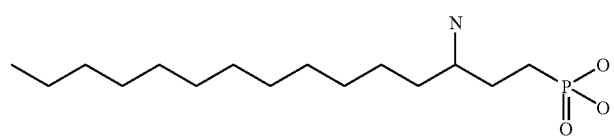 |
| 33 | 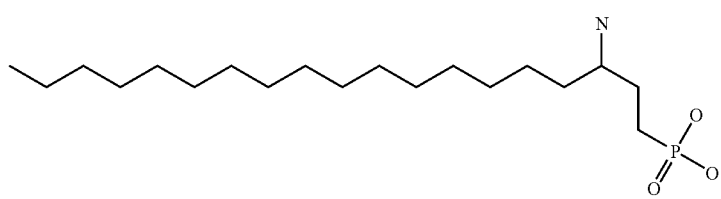 |
| 34 | 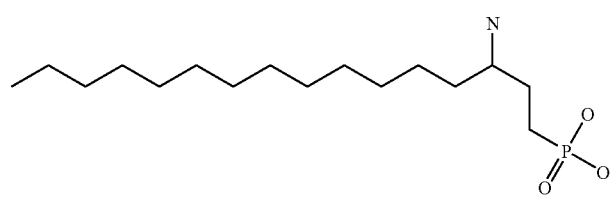 |
| 35 | 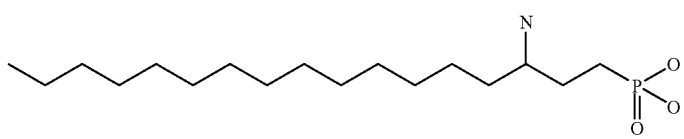 |
| 36 | 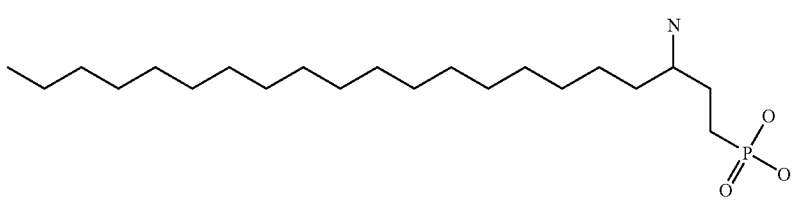 |
| 37 | 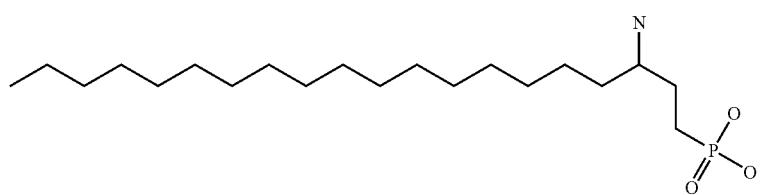 |

The invention is described using the following definitions unless otherwise indicated.

The term "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl, cyclopropyl, cyclobutyl, cyclopentyl and cyclohexyl.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "alkylthio" means alkylthio groups having the indicated number of carbon atoms of a straight, branched or cyclic configuration. $C_{1-6}$alkylthio, for example, includes methylthio, propylthio, isopropylthio, and the like.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. $C_{3-6}$alkynyl, for example, includes, propenyl, 1-methylethenyl, butenyl and the like.

The term "cycloalkyl" means mono-, bi- or tri-cyclic structures, optionally combined with linear or branched structures, the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

The term "aryl" is defined as a mono- or bi-cyclic aromatic ring system and includes, for example, phenyl, naphthyl, and the like.

The term "aralkyl" means an alkyl group as defined above of 1 to 6 carbon atoms with an aryl group as defined above substituted for one of the alkyl hydrogen atoms, for example, benzyl and the like.

The term "aryloxy" means an aryl group as defined above attached to a molecule by an oxygen atom (aryl-O) and includes, for example, phenoxy, naphthoxy and the like.

The term "aralkoxy" means an aralkyl group as defined above attached to a molecule by an oxygen atom (aralkyl-O) and includes, for example, benzyloxy, and the like.

The term "arylthio" is defined as an aryl group as defined above attached to a molecule by an sulfur atom (aryl-S) and includes, for example, thiophenyoxy, thionaphthoxy and the like.

The term "aroyl" means an aryl group as defined above attached to a molecule by an carbonyl group (aryl-C(O)—) and includes, for example, benzoyl, naphthoyl and the like.

The term "aroyloxy" means an aroyl group as defined above attached to a molecule by an oxygen atom (aroyl-O) and includes, for example, benzoyloxy or benzoxy, naphthoyloxy and the like.

The term "HET" is defined as a 5- to 10-membered aromatic, partially aromatic or non-aromatic mono- or bicyclic ring, containing 1-5 heteroatoms selected from 0, S and N, and optionally substituted with 1-2 oxo groups. Preferably, "HET" is a 5- or 6-membered aromatic or non-aromatic monocyclic ring containing 1-3 heteroatoms selected from O, S and N, for example, pyridine, pyrimidine, pyridazine, furan, thiophene, thiazole, oxazole, isooxazole and the like, or heterocycle is a 9- or 10-membered aromatic or partially aromatic bicyclic ring containing 1-3 heteroatoms selected from O, S, and N, for example, benzofuran, benzothiophene, indole, pyranopyrrole, benzopyran, quionoline, benzocyclohexyl, naphtyridine and the like. "HET" also includes the following: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrimidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

A preferred group of HET is as follows:

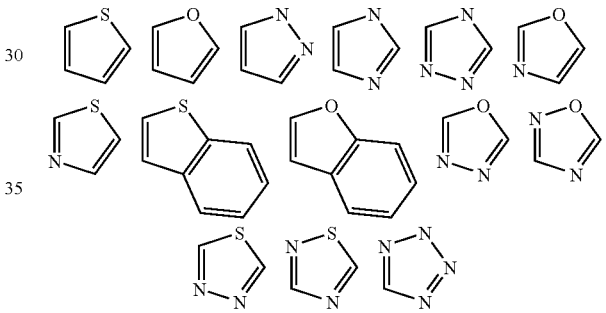

The term "treating" encompasses not only treating a patient to relieve the patient of the signs and symptoms of the disease or condition but also prophylactically treating an asymptomatic patient to prevent the onset or progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The invention described herein includes pharmaceutically acceptable salts and hydrates. Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydroscopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or pamoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

For purposes of this Specification, "pharmaceutically acceptable hydrate" means the compounds of the instant invention crystallized with one or more molecules of water to form a hydrated form.

The invention also includes the compounds falling within Formula I in the form of one or more stereoisomers, in substantially pure form or in the form of a mixture of stereoisomers. All such isomers are encompassed within the present invention.

By virtue of their $S1P_1$/Edg1 agonist activity, the compounds of the present invention are immunoregulatory agents useful for treating or preventing autoimmune or chronic inflammatory diseases. The compounds of the present invention are useful to suppress the immune system in instances where immunosuppression is in order, such as in bone marrow, organ or transplant rejection, autoimmune and chronic inflammatory diseases, including systemic lupus erythematosis, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma.

More particularly, the compounds of the present invention are useful to treat or prevent a disease or disorder selected from the group consisting of: transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scieroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderrna and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-$C_4$ release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, trauma, and chronic bacterial infection.

Also embodied within the present invention is a method of preventing or treating resistance to transplantation or transplantation rejection of organs or tissues in a mammalian patient in need thereof, which comprises administering a therapeutically effective amount of the compound of Formula I.

A method of suppressing the immune system in a mammalian patient in need thereof, which comprises administering to the patient an immune system suppressing amount of the compound of Formula I is yet another embodiment.

Most particularly, the method described herein encompasses a method of treating or preventing bone marrow or organ transplant rejection which is comprised of administering to a mammalian patient in need of such treatment or prevention a compound of Formula I, or a pharmaceutically acceptable salt or hydrate thereof, in an amount that is effective for treating or preventing bone marrow or organ transplant rejection.

Furthermore, a preferred group of compounds of the present invention are agonists of the $S1P_1$/Edg1 receptor having selectivity over $S1P_3$/Edg3 receptor. An Edg1 selective agonist has advantages over current therapies and extends the therapeutic window of lymphocytes sequestration agents, allowing better tolerability with higher dosing and thus improving efficacy as monotherapy. The following compounds possesses a selectivity for the $S1P_1$/Edg1 receptor over the $S1PR_3$/Edg3 receptor of at least 20 fold as measured by the ratio of $EC_{50}$ for the $S1P_1$/Edg1 receptor to the $EC_{50}$ for the $S1P_3$/Edg3 receptor as evaluated in the $^{35}$S-GTPγS binding assay and possesses an $EC_{50}$ for binding to the $S1P_1$/Edg1 receptor of 100 nM or less as evaluated by the $^{35}$S-GTPγS binding assay:

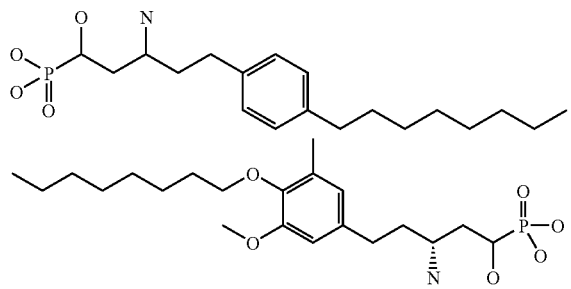

The present invention also includes a pharmaceutical formulation comprising a pharmaceutically acceptable carrier and the compound of Formula I or a pharmaceutically acceptable salt or hydrate thereof. A preferred embodiment of the formulation is one where a second immunosuppressive agent is also included. Examples of such second immunosuppressive agents are, but are not limited to azathioprine, brequinar sodium, deoxyspergualin, mizaribine, mycophenolic acid morpholino ester, cyclosporin, FK-506, rapamycin and FTY720.

The present compounds, including salts and hydrates thereof, are useful in the treatment of autoimmune diseases, including the prevention of rejection of bone marrow transplant, foreign organ transplants and/or related afflictions, diseases and illnesses.

The compounds of this invention can be administered by any means that effects contact of the active ingredient compound with the site of action in the body of a warm-blooded animal. For example, administration, can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 1 to 100 milligrams per day in one or more applications is effective to obtain desired results. These dosages are the effective amounts for the treatment of autoimmune diseases, the prevention of rejection of foreign organ transplants and/or related afflictions, diseases and illnesses.

The active ingredient can be administered orally in solid dosage forms, such as capsules, tablets, troches, dragees, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene gycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Methods of Synthesis

A method to prepare compounds of Formula I and Formula II of the present invention in which m=1, $R_1=R_2=H$ and $A=-OPO_3H_2$ is shown in Scheme 1. Vicinal amino alcohols of the structure i or v are commercially available or are readily obtained from the corresponding α-amino acids using methods commonly known to those skilled in the art. Protection of the amino group can be carried out by reacting i with an alkyl chloroformnate (e.g., $R_a$=ethyl, benzyl) or a di-alkyl dicarbonate (e.g., $R_a$=t-butyl) in the presence of a base (e.g., triethylamine, N,N-diisopropylethylamine, pyridine, potassium bicarbonate) in a suitable solvent (e.g., methylene chloride, acetonitrile, THF) to give ii. Phosphorylation can be carried out by treating ii with a N,N-dialkylamino dialkylphosphite (e.g., diethylamino dibenzylphosphite, diisopropylamino dibenzylphosphite) and catalytic 1H-tetrazole in an appropriate solvent (e.g., $CH_2Cl_2$, acetonitrile) followed by an oxidizing agent (e.g., 3-chloro peroxybenzoic acid, peracetic acid, 4-methylmorpholine N-oxide) to give phosphate ester iii. Removal of the protecting groups of iii can afford phosphate iv. In cases where $R_a=R_b=-CH_2Ph$, this can be done by treating iii with sodium in liquid ammonia. Alternatively, this can be done by stirring iii in a solution of water and alcohol (e.g., methanol, ethanol) in the presence of palladium or platinum catalyst under an atmosphere of hydrogen gas. If vicinal amino alcohol v is used as the starting material, an analogous sequence of steps can give phosphate vi.

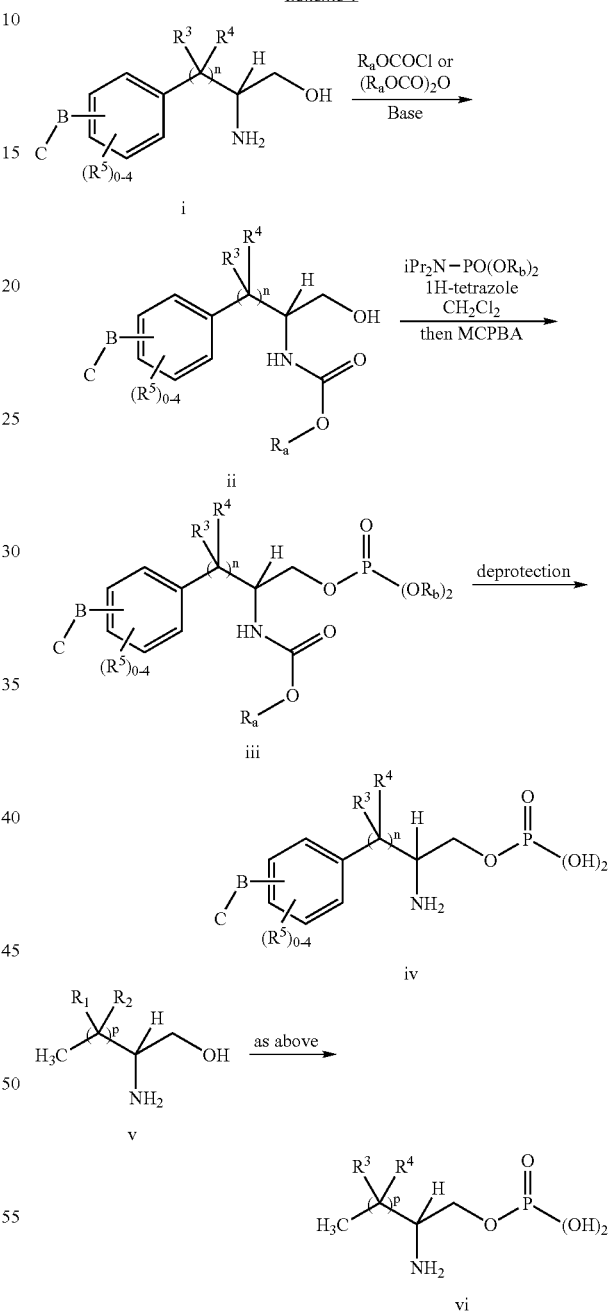

Scheme 1

A method to prepare compounds of Formula I in the present invention where m=2, the carbon atoms are joined by a double bond and $A=-PO_3H_2$ is shown in Scheme 2. Intermediate ii can be oxidized to aldehyde vii by adding ii to a mixture of oxalyl chloride and dimethylsulfoxide in methylene chloride at −78° C. followed by treatment with N,N-diisopropylethylamine then warming to ambient temperature. Other methods to effect this oxidation can involve treating ii with tetrapropylammonium peruthenate and 4-(methyl)morpholine N-oxide in solvent (e.g., methylene chloride, acetonitrile) or treating ii with the Dess-Martin periodinane in methylene chloride. Chain extension can be carried out by treating vii with tetraethyl methylenebis (phosphonate) in the presence of a suitable base (sodium bis(trimethylsilyl)amide, lithium diisopropylamide) in solvent (THF, diethyl ether) to give viii. Global deprotection of viii can be carried out by reacting viii with trimethylsilyl bromide or trimethylsilyl iodide in a suitable solvent (e.g., methylene chloride, chloroform, acetonitrile) at or above room temperature to give ix.

Alternatively, warming viii in strong aqueous acid (hydrochloric acid, sulfuric acid) can give ix.

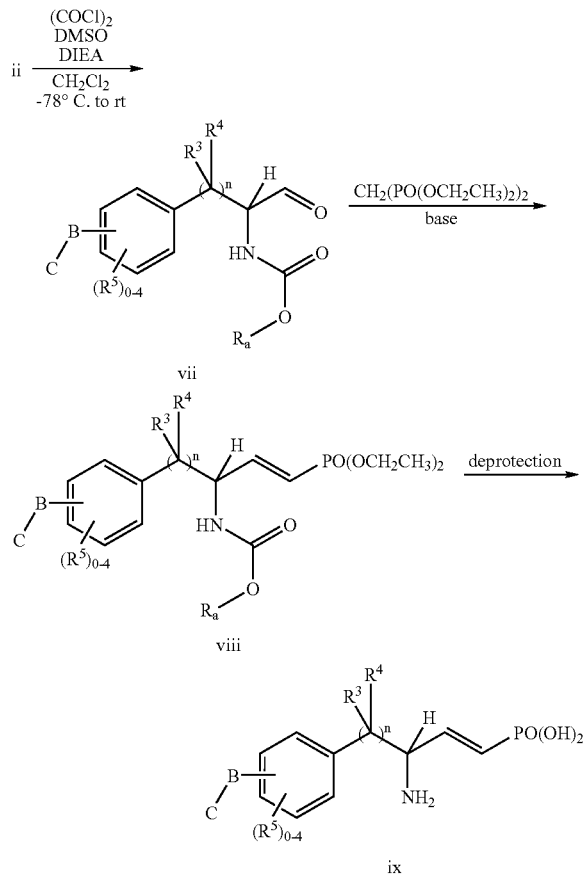

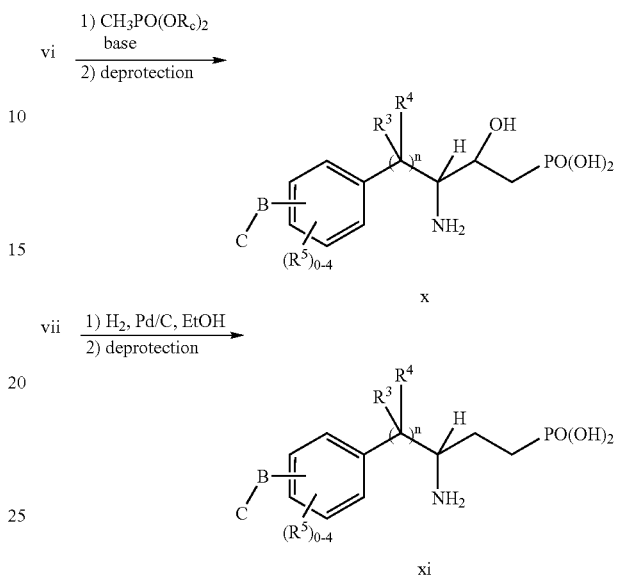

Scheme 3 depicts how some other compounds in the current invention can be prepared starting from some of intermediates described in Scheme 2. Compounds (Formula I) in the present invention where m=2, $R_1$=—OH for the carbon next to that bearing the primary amino group and A=—$PO_3H_2$ can be prepared by treating vi with a dialkyl methylphosphonate in the presence of a strong base (e.g., lithium diisopropylamide, sodium bis(trimethylsilyl)amide) in a suitable solvent (THF, 1,2-dimethoxyethane) at or below room temperature followed by deprotection using analogous to those described above to convert viii to ix. Compounds (Formula I) in the present invention where m=2, $R_1$=$R_2$=H and A=—$PO_3H_2$ can be prepared by reducing the double bond of viii using catalytic hydrogenation followed by deprotection using analogous to those described above to convert viii to ix.

A method to prepare enantiopure compounds of Formula I of the present invention in which m=2, n=2, A=—$PO_3H_2$ and $R_1$=—OH for the carbon adjacent to the phosphonic acid group is shown in Scheme 4. Freidel-Crafts acylation of a substituted arene xii can be carried out by treatment with either enantiomer of 2-(N-trifluoroacetamido)succinic anhydride ((R)-enantiomer shown) in the presence of a strong Lewis acid (e.g., $AlCl_3$) in a suitable solvent (methylene chloride, 1,2-dichloroethane) to give xiii. Reduction of the ketone functionality of xiii can be carried out with hydrogen gas (1 atm or above) in the presence of catalyst (e.g., Pd/C, Pt/C) in an appropriate solvent (MeOH, HOAc) to give xiv. Reduction of xiii can also be carried out by using a reducing agent ($NaBH_4$, triethylsilane) in the presence of acid (trifluoroacetic acid, trifluoromethanesulfonic acid) to give xiv. Treating xiv with base (NaOH, KOH) in an appropriate solvent (e.g., water, methanol, dioxane) followed by di-t-butyl dicarbonate can give carbamate protected intermediate xv. Chain extension can be accomplished by converting xv to the corresponding diazoketone followed by treatment with a silver (I) salt (e.g., silver benzoate, silver oxide) in the presence of a tertiary amine base (triethylamine, N,N-diisopropylethylamine, DBU) in an alcohol solvent to give ester xvi. Conversion of xvi to xvii can be carried out in two steps by first reducing xvi to corresponding alcohol (DIBALH, 0° C., Red-Al, toluene, −78° C.) followed by Swern oxidation to aldehyde xvii. The oxidation could also be carried out by treating the intermediate alcohol with 4-(methyl)morpholine N-oxide and catalytic tetrapropylammonium peruthenate in an appropriate solvent (methylene chloride, acetonitrile) or by treating the intermediate alcohol with the Dess-Martin periodinane in methylene chloride solvent. Alternatively xvii could be directly obtained from xvi by treatment with DIBALH at −78° C. in an appropriate solvent (methylene chloride, THF, toluene). Reacting xvii with a dialkyl phosphite in the presence of a base (e.g., sodium bis(trimethylsilyl)amide, lithium diisopropylamide, triethylamine) in an appropriate solvent (e.g., THF, $CH_2Cl_2$)

followed by deprotection using the conditions described above to convert viii to ix. The diastereomers of xviii can be separated either before or after the final deprotection to give enantiomerically pure products.

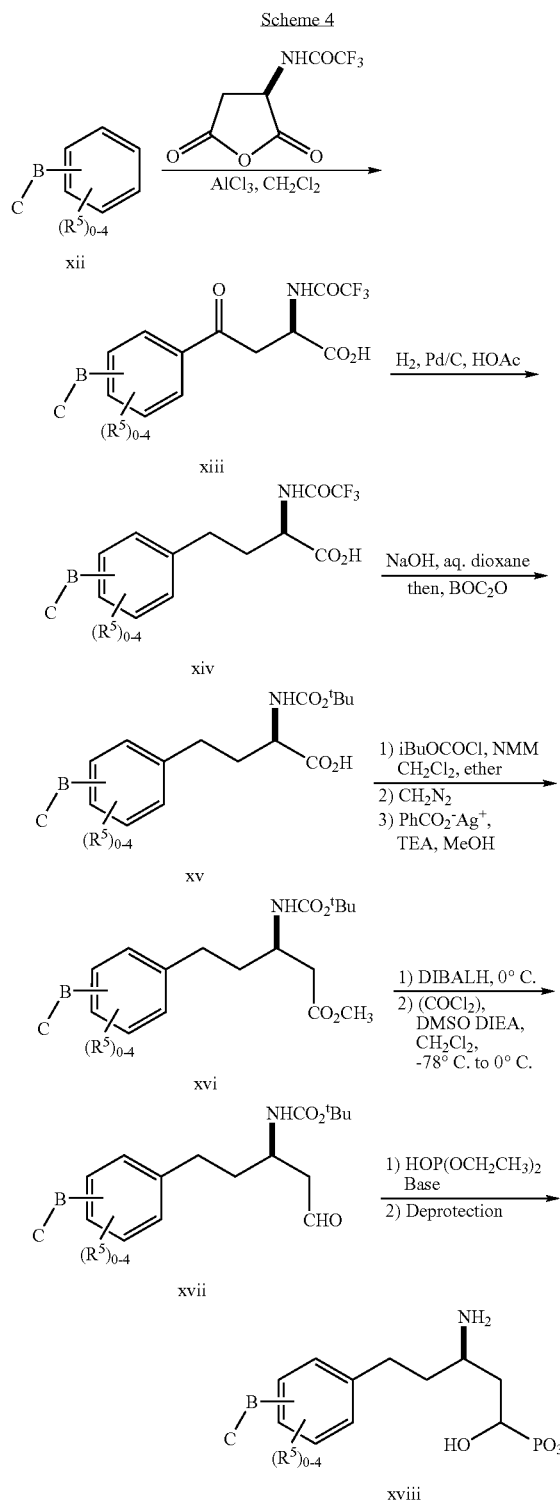

An alternative method to prepare compounds in the present invention in which m=2, n=2, A=—PO$_3$H$_2$ and R$_1$=—OH for the carbon adjacent to the phosphonic acid group is shown in Scheme 5. Vinyl oxazolidinone xix can be treated with a dialkyl borane (e.g., 9-BBN, dicyclohexylborane) in an appropriate solvent (THF, 1,2-dimethoxyethane, toluene) at or above ambient temperature followed by a substituted aryl chloride, bromide, iodide or triflate and a palladium(0) catalyst (e.g., tetrakis(triphenyl-phosphine) palladium) at or above ambient temperature to give xx. Acid catalyzed acteonide cleavage can convert xx to alcohol xxi. Chain extension can be carried out by converting xxi to the nitrile via the mesylate followed by reduction with DIBALH. Alternatively, xxi could be oxidized to the carboxylic acid, esterified to the methyl ester using diazomethane in ether or trimethylsilyldiazomethane in MeOH then converted to xxii using the same sequence of reactions described in Scheme 4 to convert xvi to xvii. Conversion of xxii to xviii can be carried out using reactions analogous to those described in Scheme 4 to convert xvii to xviii.

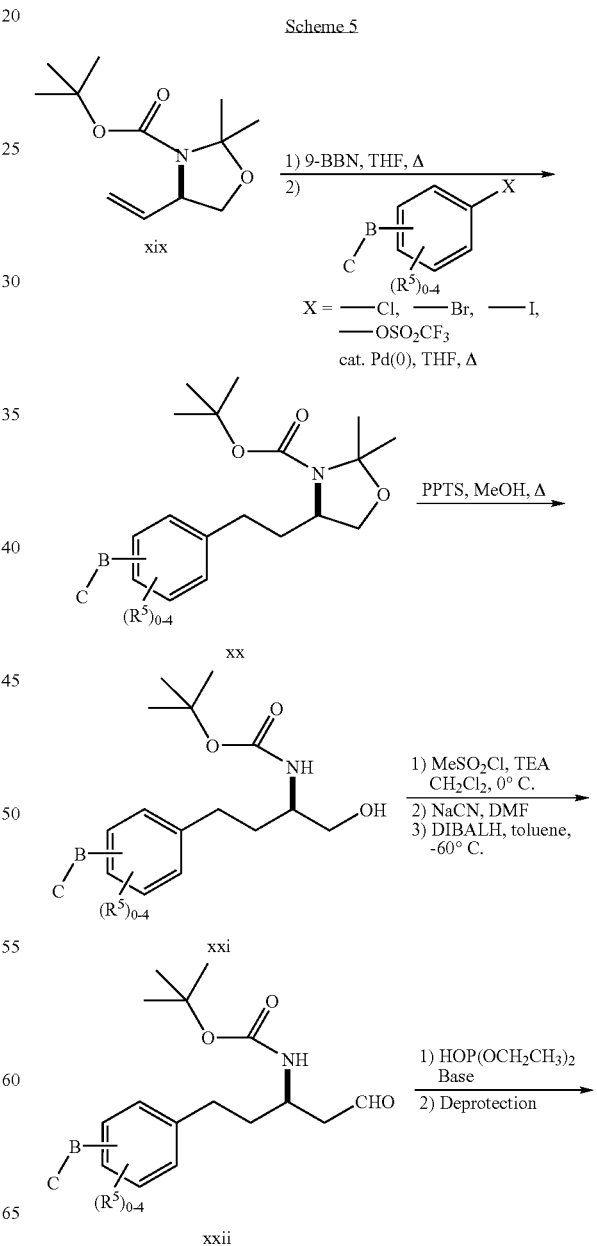

-continued

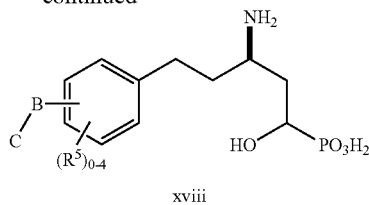

xviii

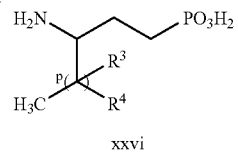

xxvi

A method to prepare compounds of Formula II of the present invention in which m=2 and A=—PO$_3$H$_2$ is shown in Scheme 6. Triethyl 4-phosphonobutyrate can be treated with a strong base (lithium diisopropylamide, sodium bis(trimethylsilyl)amide, potassium bis(trimethylsilyl)amide) in an appropriate solvent (THF, 1,2-dimethoxyethane, 1,4-dioxane) at or below ambient temperature followed by an alkyl chloride, bromide, iodide of triflate to afford xxiii. Selective saponification of the carboxylate ester of xxiii can be carried out with sodium hydroxide in aqueous methanol to carboxylic acid xxiv. Conversion of xxiv to protected amine xxv can be carried out via a Curtius rearrangement; the carboxylate is converted to the acyl azide via the mixed anhydride or acid chloride, then thermal rearrangement to the isocyanate and trapping with an alcohol affords carbamate xxv.

Global deprotection of xxv can be carried out by reacting viii with trimethylsilyl bromide or trimethylsilyl iodide in a suitable solvent (e.g., methylene chloride, chloroform, acetonitrile) at or above room temperature to give xxvi. Alternatively, warming xxv in strong aqueous acid (hydrochloric acid, sulfuric acid) can give xxvi.

Scheme 6

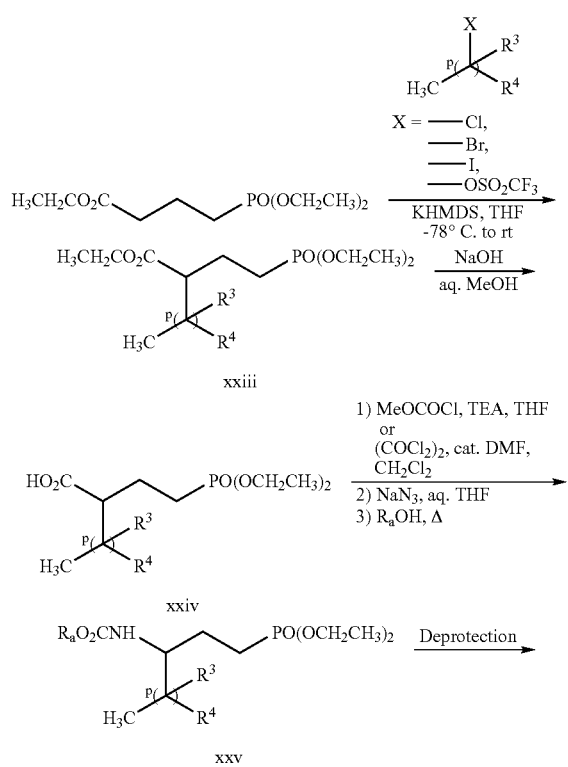

Methods for preparing the compounds of this invention are further illustrated in the following examples. Alternative routes will be easily discernible to practitioners in the field.

General Methods

Concentration of solutions was carried out on a rotary evaporator under reduced pressure. Conventional flash chromatography was carried out on silica gel (230-400 mesh). Flash chromatography was also carried out using a Biotage Flash Chromatography apparatus (Dyax Corp.) on silica gel (32-63 mM, 60 Å pore size) in pre-packed cartridges of the size noted. NMR spectra were obtained in CDCl$_3$ solution unless otherwise noted. Coupling constants (J) are in hertz (Hz). Abbreviations: diethyl ether (ether), triethylamine (TEA), N,N-diisopropylethylamine (DIEA), tetrahydrofuran (THF), saturated aqueous (sat'd), room temperature (rt), hour(s) (h), minute(s) (min).

HPLC Methods

HPLC A: Analytical Sales and Service Armor C8, 5 µ, 4.6 mm×50 mm column, gradient 10:90→90:10 v/v CH$_3$CN:H$_2$O+0.05% TFA over 4 min, then hold at 90:10 v/v CH$_3$CN:H$_2$O+0.05% TFA for4 min; 2.5 mL/min, 210 nm.

HPLC B: YMC ODS A, 5 µ, 4.6×50 mm column, gradient 10:90→95:5 v/v CH$_3$CN:H$_2$O+0.05% TFA over 4.5 min, then hold at 95:5 v/v CH$_3$CN:H$_2$O+0.05% TFA for 1.5 min; 2.5 mL/min, 210 nm.

HPLC C: Analytical Sales and Service Armor C8, 5 µ, 20 mm×10 cm column, gradient 10:90→90:10 v/v CH$_3$CN:H$_2$O+0.05% TFA over 12 min, then hold at 90:10 v/v CH$_3$CN:H$_2$O+0.05% TFA for4 min; 10 mL/min, 210 nm.

PREPARATION OF EXAMPLES

Example 1

(+/−)-2-Amino-4-(4-(octylphenyl))butanol, O-phosphate

Step A: (+/−)-2-Amino-4-(4-octylphenyl)butanoic acid

A mixture of 13.25 g (30.6 mmol) of diethyl 2-acetamido-2-(2-(4-octylphenyl)ethyl)propandioate (prepared according to the procedure described by Durand, et.al., *Synthesis*, 2000, 505-506, which is hereby incorporated by reference in its entirety) and 75 mL of concentrated HCL were stirred at 100° C. for 16 h. The mixture was cooled and 75 g of ice was added. The mixture was neutralized (pH=7) with 5 N NaOH. The precipitate was filtered, rinsed with water and dried to afford 8.9 g of the title compound: HPLC B: 2.68 min; ESI-MS 292 (M+H).

Step B: (+/−)-2-Benzyloxycarbonylamido-4-(4-octylphenyl)butanoic acid

A solution of 510 mg (1.75 mmol) of (+/−)-2-amino4-(4-octylphenyl)butanoic acid (from EXAMPLE 1, Step A) in 10 mL of 1:1 v/v dioxane/1 N NaOH was treated with 0.25 mL (1.75 mmol) of benzyl chloroformate and the resulting mixture was stirred at rt for 2 h. The mixture was extracted with 50 mL of 10:1 v/v EtOAc/iPrOH and 2×50 mL of $CH_2Cl_2$. The organics were combined, dried and concentrated. Flash chromatography on a Biotage 40S cartridge using 4:1 v/v hexanes/EtOAc +1% HOAc as the eluant afforded 525 mg (70%) of the title compound: HPLC B: 4.74 min; ESI-MS 382 ($M-CO_2+H$).

Step C: (+/−)-2-Benzyloxycarbonylamido-4-(4-octylphenyl)butanol

A mixture of 525 mg (1.2 mmol) of (+/−)-2-benzyloxycarbonylamido-4-(4-octylphenyl)butanoic acid and 0.18 mL (1.3 mmol) of TEA in 10 mL of THF at 0° C. was treated with 0.17 mL (1.3 mmol) of isobutyl chloroformate and stirred cold for 30 min. The mixture was gradually filtered into a cooled (0° C.) solution of 300 mg (7.9 mmol) of sodium borohydride in 20 mL of water and stirred cold for 2 h. The reaction was quenched with 20 mL of 1 N HCl, then extracted with 75 mL of EtOAc. The extract was dried and concentrated. Flash chromatography on a Biotage 40S cartridge using 4:1 v/v hexanes/acetone as the eluant afforded 390 mg (79%) of the title compound.

Step D: (+/−)-1-Dibenzylphosphoryloxy-2-benzyloxycarbonylamido-4-(4-octylphenyl)butane A solution of 132 mg (0.32 mmol) of (+/−)-2-benzyloxycarbonylamido-4-(4-octylphenyl)butanol (from EXAMPLE 1, Step C), 134 mg (0.39 mmol) of dibenzyl diisopropylphosphoramidite and 36 mg (0.52 mmol) of 1H-tetrazole in 3 mL of $CH_2Cl_2$ was stirred at )° C. for 1 h. The mixture was treated with 99 mg (0.4 mmol) of 70% MCPBA. The cooling bath was removed and the resulting mixture was stirred at rt for 1 h. The reaction was quenched with 5 mL of sat'd $NaHCO_3$, then partitioned between 40 mL of ether and 20 mL of water. The organic layer was separated, dried and concentrated. Flash chromatography on a Biotage 40S cartridge using 3:2 hexanes/ether as the eluant afforded 158 mg (73%) of the title compound: $^1$H NMR (500 Mhz) δ 0.88 (t, J=7.0, 3H), 1.26-1.30 (12H), 1.55-1.59 (m, 2H), 1.70-1.75 (m, 2H), 2.53-2.58 (4H), 3.95-4.00 (m, 1H), 4.90 (d, J=9.0, 1H), 4.96-5.04 (6H), 5.07 (q, J=12.5, 2H), 7.00-7.30 (15H).

Step E: (+/−)-2-Amino-4-(4-(octylphenyl))butanol, O-phosphate

A solution of 157 mg (0.23 mmol) of (+/−)-1-dibenzylphosphoryloxy-2-benzyloxycarbonylamido4-(4-octylphenyl)butane (from EXAMPLE 1, Step D) in 1 mL of THF was added to a mixture of 185 mg (7.7 mmol) of sodium metal in 10 mL of liquid ammonia at −33° C. The mixture was stirred for 1.5 h, then quenched with 5 g ice/5 mL of water. The mixture was partitioned between 50 mL of ether and 20 mL of water. The aqueous layer was separated and neutralized (pH=7) with 1 N HCl. The precipitate was filtered, washed with water, washed with MeOH and dried to afford 60 mg (73%) of the title compound: HPLC B: 2.90 min; ESI-MS 357 (M+H).

Example 2

(+/−)-trans-3-Amino-4-(4-octylphenyl)but-1-enyl phosphonic acid

Step A: (+/−)-2-(t-butoxycarbonylamido)-4-(4-octylphenyl)butanoic acid

A solution of 9.8 g (30.6 mmol) of (+/−)-2-amino-4-(4-octylphenyl)butanoic acid (from EXAMPLE 1, Step A) in 150 mL of 1:1 v/v dioxane/1 N NaOH was treated with 10 g (45.8 mmol) of di-t-butyl dicarbonate and stirred at rt for 1 h. The mixture was partitioned between 550 mL of 10:1 v/v EtOAc/iPrOH and 200 mL of 1 N HCl. The organic layer was separated, dried and concentrated. Flash chromatography on a Biotage 75S cartridge using 4:1 v/v heptane/EtOAc (2.5 L), then 4:1 v/v heptane/EtOAc+1% HOAc (5 L) as the eluant afforded 12.0 g (100%) of the title compound: HPLC B: 4.82 min; ESI-MS 292 (M-BOC+H).

Step B: (+/−)-2-(t-Butoxycarbonylamido)-4-(4-octylphenyl)butanol

The title compound was prepared from (+/−)-2-(t-butoxycarbonylamido)-4-(4-octylphenyl)butanoic acid (from EXAMPLE 2, Step A) using a procedure analogous to that described in EXAMPLE 1, Step C: $^1$H NMR (500 Mhz) δ 0.88 (t, J=6.5, 3H), 1.25-1.30 (12H), 1.45 (s, 9H), 1.55-1.62 (m, 2H), 1.72-177 (m, 1H), 1.79-1.85 (m, 1H), 2.33 (br s, 1H), 2.56 (t, J=8.5, 2H), 2.61-2.71 (m, 4H), 3.56-3.58 (m, 1H), 3.65-3.69 (m, 2H), 4.644.66 (br s, 1H), 7.09 (app s, 4H).

Step C: (+/−)-2-(t-butoxycarbonylamido)4-(4-octylphenyl)butanal

A solution of 0.21 mL (2.4 mmol) of oxalyl chloride in 8 mL of $CH_2Cl_2$ at −78° C. was treated with 0.26 mL (3.6 mmol) of dimethylsulfoxide. The resulting mixture was stirred cold for 5 min, then treated with a solution of 460 mg (1.2 mmol) of (+/−)-2-(t-butoxycarbonylamido)4-(4-octylphenyl)butanol (from EXAMPLE 2, Step B) in 3 mL of $CH_2Cl_2$. The resulting mixture was stirred cold for 30 min, then treated with 1.50 mL (8.6 mmol) of DIEA. The cooling bath was removed and the reaction mixture was allowed to warm to 0° C. The reaction was quenched with 25 mL of 0.5 N $KHSO_4$, then partitioned between 50 mL of $CH_2Cl_2$ and 20 mL of water. The organic layer was separated, dried and concentrated. Flash chromatography on a Biotage 40S cartridge using 4:1 v/v hexanes/ether as the eluant afforded 388 mg (86%) of the title compound: $^1$H NMR (500 Mhz) δ 0.88 (t, J=6.5, 3H), 1.22-1.33 (12H), 1.46 (s, 9H), 1.55-1.61 (m, 2H), 1.85-1.89 (m, 1H), 1.96-2.06 (m, 1H), 1.85-1.91 (m, 1H), 2.14-2.24 (m, 1H), 2.56 (t, J=8.0, 2H), 2.60-2.70 (m, 2H), 4.24 (br s, 1H), 5.05 (br s, 1H), 7.07-7.11 (4H), 9.54 (s, 1H).

Step D: Diethyl (+/−)-trans-3-(t-butoxycarbonylamido-4-(4-octylphenyl)but-1-enyl phosphonate A solution of 432 mg (1.5 mmol) of tetraethyl methylenediphosphonate in 4 mL of THF was treated with 1.5 mL of 1.0 M sodium bis(trimethylsilyl)amide solution in THF and stirred at rt for 15 min. The resulting mixture was treated with a solution of 188 mg of (+/−)-2-(t-butoxycarbonylamido)-4-(4-octylphenyl)butanal (from EXAMPLE 2, Step C) in 2 mL of THF and stirred at rt for 30 min. The reaction was quenched with 10 mL of sat'd $NaHCO_3$, then partitioned between 40 mL of ether and 10 mL of water. The organic layer was separated, dried and concentrated. Flash chromatography on a Biotage 40S cartridge using 4:1 v/v $CH_2Cl_2$/EtOAc (1 L), then 3:2 v/v $CH_2Cl_2$/EtOAc (1 L) as the eluant afforded 218 mg (86%) of the title compound: $^1$H NMR (500 Mhz) δ 0.88 (t, J=7.0, 3H), 1.22-1.34 (12H), 1.44 (s, 9H), 1.56-1.61 (m, 1H), 1.72-1.82 (m, 1H), 1.86-1.94 (m, 1H), 2.56 (t, J=8.0, 2H), 2.61-2.67 (m, 2H), 4.04-4.10 (4H), 4.31 (br s, 1H), 4.50 (br s, 1H), 5.78 (app t, J=17.0, 1H), 6.64-6.73 (m, 1H), 7.08 (app q, J=8.0, 4H);

HPLC A: 5.43 min; HPLC B: 5.03 min; ESI-MS 510 (M+H).

Step E: (+/−)-trans-3-Amino-4-(4-octylphenyl)but-1-enyl phosphonic acid

A solution of 98 mg (0.19 mmol) of diethyl (+/−)-trans-3-(t-butoxycarbonylamido)-4-(4-octylphenyl)but-1-enyl phosphonate in 2 mL of $CH_2Cl_2$ was treated with 0.14 mL (0.8 mmol) of trimethylsilyl trifluoromethanesulfonate and stirred at rt for 15 min. The mixture was treated with 0.07 mL of (0.5 mmol) of iodotrimethylsilane and stirred at rt for 2 h. The reaction was quenched with 5 mL of MeOH, then concentrated. HPLC purification (HPLC C) afforded 57 mg (85%) of the title compound: HPLC B: 2.78 min; ESI-MS 354 (M+H).

Example 3

(+/−)-3-Amino-4-(4-octylphenyl)butyl phosphonic acid

Step A: Diethyl (+/−)-3-(-butoxycarbonylamino)-4-(4-octylphenyl)butyl phosphonate A mixture of 100 mg (0.2 mmol) of diethyl (+/−)-trans-3-(t-butoxycarbonylamido-4-(4-octylphenyl)but-1-enyl phosphonate (from EXAMPLE 2, Step D) and 40 mg of 10% palladium on carbon in 5 mL of EtOH was stirred under an atmosphere of $H_2$ for 20 h. The catalyst was filtered and the filtrate concentrated to afford 100 mg (100%) of the title compound.

Step B: (+/−)-3-Amino-4-(4-octylphenyl)butyl phosphonic acid

A solution of 100 mg (0.2 mmol) of diethyl (+/−)-3-(-butoxycarbonylamino)-4-(4-octylphenyl)butyl phosphonate (from EXAMPLE 3, Step A) in 3 mL of $CH_2Cl_2$ was treated with 0.11 mL (0.77 mmol) of iodotrimethylsilane and stirred at rt for 1 h. The reaction was quenched with 5 mL of MeOH, then concentrated. BPLC purification (HPLC C) afforded 39 mg (56%) of the title compound: HPLC A: 3.94 min; HPLC B: 2.88 min; ESI-MS 356 (M+H).

Example 4

2-Hydroxy-3-amino-4-(4-octylphenyl)butyl phosphonic acid

Step A: Diethyl 2-hydroxy-3-(-butoxycarbonylamino)-4-(4-octylphenyl)butyl phosphonate A solution of 0.17 mL (1.2 mmol) of diisopropylamine in 8 mL of THF at 0° C. was treated with 0.48 mL of 2.5 M n-butyllithium solution in hexanes. The resulting mixture was cooled to −78° C. A solution of 332 mg (1.2 mmol) of dibenzyl methylphosphonate in 1 mL of THF was added and the resulting mixture was stirred cold for 1 h. A solution of 175 mg (0.47 mmol) of (+/−)-2-(t-butoxycarbonylamido)-4-(4-octylphenyl)butanal (from EXAMPLE 2, Step C) was added and the resulting mixture was stirred cold for 2 h. The reaction was quenched with 10 mL of sat'd $NH_4Cl$ and partitioned between 50 mL of ether and 10 mL of water. The organic layer was separated, dried and concentrated. Flash chromatography on a Biotage 40S cartridge using 4:1 v/v hexanes/acetone afforded 158 mg (61%) of the title compound as a mixture of isomers: HPLC A: 5.99 min.

Step B: 2-Hydroxy-3-amino-4-(4-octylphenyl)butyl phosphonic acid

The title compound was prepared from diethyl 2-hydroxy-3-(-butoxycarbonylamino)-4-(4-octylphenyl)butyl phosphonate (from EXAMPLE 4, Step A) using a procedure analogous to that described in EXAMPLE 3, Step B: HPLC B: 2.83 min; ESI-MS 372 (M+H).

Example 5

(+/−)-3-Amino-5-(4-octylphenyl)pentanoic acid

Step A: (+/−)-1-Diazo-3-(t-butoxycarbonylamido)-5-(4-octylphenyl)pentan-2-one

A solution of 705 mg (1.8 mmol) of (+/−)-2-(t-butoxycarbonylamido)-4-(4-octylphenyl)butanoic acid (from EXAMPLE 2, Step A) and 0.26 mL (2.4 mmol) of 4-methylmorpholine in 10 mL of 1:1 v/v $CH_2Cl_2$/ether at 0° C. was treated with 0.26 mL (2.0 mmol) of isobutylchloroformate and stirred cold for 50 min. The mixture was filtered into a solution of diazomethane (7 mmol) in 15 mL of ether at 0° C. The cooling bath was removed and the mixture was allowed to stand at rt for 20 h. Acetic acid (0.5 mL) was added to quench residual diazomethane. Toluene (20 mL) was added and the mixture concentrated. Flash chromatography on a Biotage 40S cartridge using 3:1 v/v hexanes/EtOAc afforded 696 mg (86%) of the title compound.

Step B: (+/−)-Methyl 3-(t-butoxycarbonylamido)-5-(4-octylphenyl)pentanoate

A solution of 694 mg (1.6 mmol) of (+/−)-1-diazo-3-(t-butoxycarbonylamido)-5-(4-octylphenyl) pentan-2-one (from EXAMPLE 5, Step A) in 10 mL of MeOH was treated with a solution of 70 mg (0.3 mmol) of silver benzoate in 1 mL of TEA and stirred at rt for 20 min. The mixture was filtered through a pad of Celite and the filtrate was concentrated. Flash chromatography on a Biotage 40S cartridge using 9:1 v/v hexanes/EtOAc afforded 565 mg (87%) of the title compound: $^1$H NMR (500 Mhz) δ 0.88 (t, J=6.5, 3H), 1.22-1.36 (12H), 1.45 (s, 1H), 1.55-1.62 (m, 2H), 1.74-1.88 (m, 2H), 2.51-2.70 (4H), 2.55 (t, J=8, 2H), 3.67 (s, 3H), 3.90-3.98 (m, 1H), 4.97 (d, J=8.0, 1H), 7.08 (app s, 4H).

Step C: (+/−)-3-Amino-5-(4-octylphenyl)pentanoic acid

A solution of 100 mg of (+/−)-methyl 3-(t-butoxycarbonylamido)-5-(4-octylphenyl)pentanoate (from EXAMPLE 5, Step B) in 4 mL of MeOH was treated with 0.5 mL of 5 N NaOH and stirred at rt for 30 min. The mixture was concentrated and the residue was partitioned between 30 mL of EtOAc and 20 mL of 1 N HCl. The organic layer was separated, dried and concentrated. The residue was dissolved in 2 mL of $CH_2Cl_2$, cooled to 0° C. and treated with 2 mL of trifluoroacetic acid. The resulting mixture was stirred at rt for 2 h, then concentrated. The residue was triturated with ether and filtered to afford 58 mg (79%) of the title compound: HPLC B: 3.22 min; ESI-MS 306 (M+H).

Example 6

(+/−)-N-Methanesulfonyl 2-amino-4-(4-octylphenyl)butanamide, trifluoroacetate salt Step A: (+/−)-N-Methanesulfonyl 2-(t-butoxycarbonylamido)-4-(4-octylphenyl)butanamide A mixture of 110 mg (0.28 mmol) of (+/−)-2-(t-butoxycarbonylamido)-4-(4-octylphenyl)butanoic acid (from EXAMPLE 2, Step A) and 46 mg (0.28 mmol) of N,N-carbonyldiimidazole in 2.5 mL of THF was heated at reflux for 1 h. The resulting mixture was cooled, treated with 35 mg (0.37 mmol) methane sulfonamide and 0.075 mL of DBU and stirred at rt for 20 h. The mixture was partitioned 40 mL of EtOAc and 20 mL of 1 N HCl and the layers were separated. The organic layer was dried and concentrated. Flash chromatography on a Biotage 40S cartridge using 10:1 v/v CH$_2$Cl$_2$/EtOAc+0.5% HOAc afforded 107 mg (82%) of the title compound: $^1$H NMR (400 Mhz) δ 0.88 (t, J=7.2, 3H), 1.22-1.36 (12H), 1.46 (s, 9H), 1.54-1.62 (m, 2H), 1.88-1.98 (m, 1H), 2.14-2.24 (m, 1H), 3.26 (s, 3H), 4.08 (br s, 1H), 4.99 (br s, 1H), 7.03-7.18 (4H), 9.3 (br s, 1H).

Step B: (+/−)-N-Methanesulfonyl 2-amino-4-(4-octylphenyl)butanamide, trifluoroacetate salt A solution of 105 mg (0.2 mmol) (+/−)-N-methanesulfonyl 2-(t-butoxycarbonylamido)-4-(4-octylphenyl)butanamide (from EXAMPLE 6, Step A) in 3 mL of CH$_2$Cl$_2$ at 0° C. was treated with 3 mL of trifluoroacetic acid. The resulting mixture was stirred at rt for 1.5 h then concentrated to afford 108 mg (100%) of the title compound: $^1$H NMR (500 Mhz, CD$_3$OD) δ 0.88 (t, J=7.0, 3H), 1.22-1.36 (12H), 1.56-1.62 (m, 2H), 2.18-2.22 (m, 2H), 3.26 (s, 3H), 3.96-4.00 (m, 1H); HPLC B: 3.09 min; ESI-MS 369 (M+H).

Example 7

(+/−)-N-(1H-tetrazol-5-yl) 2-amino-4-(4-octylphenyl)butanamide, hydrochloride salt Step A: (+/−)-N-(1H-tetrazol-5-yl) 2-(t-butoxycarbonylamido)-4-(4-octylphenyl)butanamide A mixture of 98 mg (0.25 mmol) of (+/−)-2-(t-butoxycarbonylamido)-4-(4-octylphenyl)butanoic acid (from EXAMPLE 2, Step A) and 41 mg (0.25 mmol) of N,N-carbonyidiimidazole in 2.5 mL of THF was heated at reflux for 1 h. The mixture was treated with 40 mg (0.39 mmol) of 5-aminotetrazole monohydrate and heated at reflux for 3 h. The mixture was cooled and partitioned between 40 mL of EtOAc and 20 mL of 1 N HCl. The organic layer was separated, dried and concentrated. Flash chromatography on a Biotage 40S cartridge using 2:1 v/v hexanes/EtOAc+1% HOAc, then 2:1 CH$_2$Cl$_2$/EtOAc+1% HOAc, then 20:1 EtOAc/MeOH+2% HOAc as the eluant afforded 78 mg (68%) of the title compound:
$^1$H NMR (500 Mhz, CD$_3$OD) δ 0.88 (t, J=7.0, 3H), 1.24-1.34 (12H), 1.45 (s, 9H), 1.54-1.60 (m, 2H), 1.93-2.02 (m, 1H), 2.04-2.14 (m, 1H), 2.53 (t, J=8.0, 2H), 2.61-2.68 (m, 1H), 2.70-2.80 (m, 1H), 4.23 (br s, 1H), 7.07 (app q, J=8.0, 4H); HPLC A: 4.51 min; HPLC B: 4.53 min; ESI-MS 459 (M+H).

Step B: (+/−)-N-(1H-tetrazol-5-yl) 2-amino-4-(4-octylphenyl)butanamide, hydrochloride salt A solution of 78 mg (0.17 mmol) of (+/−)-N-(1H-tetrazol-5-yl) 2-(t-butoxycarbonylamido)-4-(4-octylphenyl)butanamide (from EXAMPLE 7, Step A) in 8 mL of 0.5 N HCl in MeOH was stirred at rt for 72 h. The solution was concentrated and the residue was triturated with ether. The resulting solid was filtered and dried to afford 58 mg (86%) of the title compound: HPLC B: 2.67 min; ESI-MS 359 (M+H).

Example 8

(+/−)-3-Amino-5-(4-octylphenyl)pentanesulfonic acid

Step A: (+/−)-3-(t-butoxycarbonylamido)-5-(4-octylphenyl)pentanol

A solution of 345 mg (0.82 mmol) of (+/−)-methyl 3-(t-butoxycarbonylamido)-5-(4-octylphenyl)pentanoate (from EXAMPLE 5, Step B) in 8 mL of CH$_2$Cl$_2$ at −78° C. was treated with 2.0 mL of 1.0 M diisobutylaluminum hydride solution in CH$_2$Cl$_2$. Resulting mixture was warmed to 0° C. and stirred for 2 h. The reaction was quenched with 5 mL of sat'd Rochelle salt soln and partitioned between 50 mL of ether and 20 mL of 1 N NaOH. The organic layer was separated, dried and concentrated. Flash chromatography on a Biotage 40S cartridge using 3:1 hexanes/EtOAc afforded 292 mg (91%) of the title compound.

Step B: (+/−)-1-Iodo-3-(t-butoxycarbonylamido)-5-(4-octylphenyl)pentane

A solution of 131 mg (0.5 mmol) of triphenylphosphine and 34 mg (0.5 mmol) of imidazole in 5 mL of CH$_2$Cl$_2$ was treated with 126 mg (0.5 mmol) of iodine and stirred at rt for 30 min. The resulting mixture was treated with 108 mg (0.28 mmol) of 3-(t-butoxycarbonylamido)-5-(4-octylphenyl)pentanol (from EXAMPLE 8, Step A) and stirred for 1 h. The reaction was quenched with 5 mL of sat'd NaHCO$_3$ and partitioned between 40 mL of ether and 20 mL of water The organic layer was separated and dried. Flash chromatography on a Biotage 40S cartridge using 9:1 v/v hexanes/ether afforded 105 mg (76%) of the title compound: $^1$H NMR (500 Mhz) δ 0.88 (t, J=7.0, 3H), 1.22-1.38 (12H), 1.45 (s, 9H), 1.55-1.62 (m, 2H), 1.64-1.82 (2 h), 1.94-2.12 (2H), 2.56 (t, J=7.5, 2H), 2.55-2.66 (m, 2H), 3.12-3.24 (2H), 3.64 (br s, 1H), 4.31 (d, J=9.0, 1H) 7.08 (app s, 4H); HPLC A: 5.57 min.

Step C: (+/−)-3-Amino-5-(4-octylphenyl)pentanesulfonic acid

A mixture of 102 mg (0.2 mmol) of 1-iodo-3-(t-butoxycarbonylamido)-5-(4-octylphenyl)pentane (from EXAMPLE 8, Step B) and 252 mg (2 mmol) of sodium sulfite in 4 mL of 1:1 v/v EtOH/water was heated at 70° C. for 16 h. The mixture was cooled and partitioned between 10:1 v/v CH$_2$Cl$_2$/iPrOH and 1 N HCl and the layers were separated. The organic layer was dried and concentrated. The residue was dissolved in 6 mL of 1:1 v/v CH2Cl2/trifluoroacetic acid and the resulting solution was stirred at rt for 30 min. The mixture was concentrated, then dissolved in 5 mL of MeOH. The precipitate was filtered and dried to afford 30 mg (42%) of the title compound: HPLC A: 3.41 min; HPLC B: 3.14 min; ESI-MS 356 (M+H).

Example 9

(+/−)-trans-4-Amino-6-(4-octylphenyl)hex-2-enoic acid

Step A: Methyl (+/−)-trans-4-amino-6-(4-octylphenyl)hex-2-enoate

A solution of 0.24 mL (1.5 mmol) of trimethylphosphonoacetate in 5 mL of THF at 0° C. was treated with 1.5 mL of sodium bis(trimethylsilyl)amide solution in THF and stirred cold for 20 min. A solution of 365 mg (0.97 mmol) of (+/−)-2-(t-butoxycarbonylamido)-4-(4-octylphenyl)butanal (from EXAMPLE 2, Step C) was added, the cooling bath was removed and the mixture was stirred at rt for 45 min. The reaction was quenched and partitioned between 50 mL of ether and 25 mL of water. The organic layer was separated, dried and concentrated. Flash chromatography on a Biotage 40S cartridge using 3:1 vlv hexanes/ether afforded 300 mg (72%) of the title compound: $^1$H NMR (500 Mhz) δ 0.88 (t, J=7.0, 3H), 1.24-1.36 (12H), 1.45 (s, 9H), 1.55-1.61 (m, 2H), 1.74-1.94 (2H), 3.74 (s, 3H), 4.33 (br s, 1H), 4.52 (br s, 1H), 5.93 (dd, J=15.5, 1.0, 1H), 6.87 (dd, J=15.5, 5.0, 1H), 7.08 (app q, J=8.5, 4H).

Step B: (+/−)-trans4-Amino-6-(4-octylphenyl)hex-2-enoic acid

The title compound was prepared from methyl (+/−)-trans-4-amino-6-(4-octylphenyl)hex-2-enoate (from EXAMPLE 9, Step A) using a procedure analogous to that described in EXAMPLE 5, Step C: HPLC B: 2.90 min; ESI-MS 350 (M+H).

Example 10

(+/−)-4-Amino-6-(4-octylphenyl)hexanoic acid

Step A: Methyl (+/−)-4-(t-butoxycarbonylamido)-6-(4-octylphenyl)hexanoate

The title compound was prepared from methyl (+/−)-trans-4-amino-6-(4-octylphenyl)hex-2-enoate (from EXAMPLE 9, Step A) using a procedure analogous to that described in EXAMPLE 3, Step A.

Step B: (+/−)-4-Amino-6-(4-octylphenyl)hexanoic acid

The title compound was prepared from methyl (+/−)-4-(t-butoxycarbonylamido)-6-(4-octylphenyl)hexanoate using a procedure analogous to that described in EXAMPLE 5, Step C.

Example 11

1-(1H-Tetrazol-5-yl)-3-amino-5-(4-octylphenyl)pentanol trifluoroacetate salt

Step A: (+/−)-3-(t-butoxycarbonylamido)-5-(4-octylphenyl)pentanal

The title compound was prepared from 3-(t-butoxycarbonylamido)-5-(4-octylphenyl)pentanol (from EXAMPLE 8, Step A) using a procedure analogous to that described in EXAMPLE 2, Step C: $^1$H NMR (500 Mhz) δ 0.88 (t, J=7.0, 3H), 1.22-1.36 (12H), 1.44 (s, 9H), 1.52-1.62 (m, 2H), 1.76-1.90 (m, 2H), 2.56 (t, J=8.0, 2H), 2.60-2.74 (4H), 4.05 (br s, 1H), 4.68 (br, s)7.08-7.10 (4H), 9.74 (s, 1H).

Step B: 1-(1-(4-Methoxybenzyl)-tetrazol-5-yl)-3-(t-butylcarbonylamino-5-(4-octylphenyl)pentanol, (+/−)-Isomer 1 and (+/−)-Isomer 2

A solution of 400 mg (2.1 mmol) of 1-(4-methoxybenzyl) tetrazole in 11 mL of 10:1 v/v THF/N,N,N'N'-tetramethylethylenediamine at −100° C. was treated with 1.3 mL of 1.6 M n-butyllithium solution in hexanes and stirred cold for 10 min. The resulting mixture was treated with a solution of 260 mg (0.67 mmol) of (+/−)-3-(t-butoxycarbonylamido)-5-(4-octylphenyl)pentanal (from EXAMPLE 11, Step A) in 2 mL of THF. The mixture was allowed to gradually warm to 0° C., then was quenched with 20 mL of 1 N HCl. The quenched mixture was extracted with 70 mL of ether. The extract was separated, dried and concentrated. Flash chromatography on a Biotage 40M cartridge using 17:3 v/v hexanes/EtOAc afforded the title compound as two isomers. For (+/−)-Isomer 1 (94 mg, 24%: HPLC B: 5.25 min; ESI-MS 580 (M+H). For Isomer 2 (84 mg, 22%): HPLC B: 4.99 min; ESI-MS 580 (M+H).

Step C: 1-(1H-Tetrazol-5-yl)-3-amino-5-(4-octylphenyl) pentanol, (+/−)-Isomer 1and (+/−)-Isomer 2

A solution 89 mg (0.15 mmol) of 1-(1-(4-methoxybenzyl)-tetrazol-5-yl)-3-(t-butylcarbonylamino-5-(4-octylphenyl)pentanol, (+/−)-Isomer 1 (from EXAMPLE 11, Step B) and 0.10 mL (0.7 mmol) of iodotrimethylsilane in 3 mL of CHCl$_3$ was stirred at 50° C. for 2 h. The mixture was treated with additional iodotrimethylsilane (0.15 mL) and stirred for 2 h. The mixture was cooled, treated with 3 mL of MeOH and stirred at rt for 20 h. The mixture was concentrated. HPLC purification (HPLC C) afforded 60 mg (85%) of the title compound ((+/−)-Isomer 1) as its corresponding trifluoroacetate salt: HPLC B: 2.93 min; ESI-MS 360 (M+H).

The title compound ((+/−)-Isomer 2) was obtained similarly from 1-(1-(4-methoxybenzyl)-tetrazol-5-yl)-3-(t-butylcarbonylamino-5-(4-octylphenyl)pentanol, (+/−)-Isomer 2 (from EXAMPLE 11, Step B): HPLC B: 2.93 min; ESI-MS 360 (M+H).

Example 12

1-(R or S)-Hydroxy-3-(R)-amino-5-(4-octylphenyl) pentylphosphonic acid

Step A: 2-(R)-Trifluoroacetamido-4-oxo-4-(4-octylphenyl) butanoic acid

A suspension of 2.0 g (15.0 mmol) of aluminum chloride in 10 mL of CH$_2$Cl$_2$ was treated with 0.8 mL (15 mmol) of nitromethane, then 2.2 mL (10 mmol) of octylbenzene. The resulting homogeneous mixture was treated with 1.06 g (5.0 mmol) 2-(R)-trifluoroacetamido succinic anhydride and stirred at rt for 20 h. The mixture was quenched with 20 mL of 1 N HCl, then extracted with 150 mL of EtOAc. The extract was separated, dried and concentrated. Flash chromatography on a Biotage 40M cartridge using 9:1 v/v hexanes/EtOAc+1% HOAc, then 7:3 v/v hexanes/EtOAc+ 1% HOAc as the eluant afforded 1.90 g of impure product. Recrystallization from 20:1 hexanes/EtOAc afforded 1.41 g (70%) of the title compound: $^1$H NMR (500 Mhz) δ 0.88 (t, J=7.0, 3H), 1.22-1.38 (12H), 1.58-1.66 (m, 2H), 2.68 (t, J=8.0, 2H), 3.57 (dd, J=13.5, 4.5, 1H), 3.89 (dd, J=13.5, 4.5, 1H), 4.99-5.03 (m, 1H), 7.30 (d, J=8.5, 2H), 7.52 (d, J=8.0, 1H), 7.86 (d, J=8.5, 2H); HPLC A: 4.27 min; HPLC B: 4.32 min.

Step B: 2-(R)-Trifluoroacetamido-4-(4-octylphenyl)butanoic acid

A mixture of 8.7 g (21.7 mmol) of 2-(R)-trifluoroacetamido-4-oxo-4-(4-octylphenyl)butanoic acid (from Example 12, Step A) and 1.75 g of 10% Pd/C in 25 mL of HOAc was hydrogenated at 40 psi for 20 h. The mixture was filtered through a pad of Celite; the flask and pad were rinsed with EtOAc. Toluene was added to the filtrate and the filtrate was concentrated to afford 9.0 of the title compound which was used without further purification.

Step C: 2-(R)-(t-Butoxycarbonylamido)-4-(4-octylphenyl) butanoic acid

A solution of 9.0 g (~21.7 mmol) of crude 2-(R)-trifluoroacetamido-4-(4-octylphenyl)butanoic acid (from Example 12, Step B) in 50 mL of dioxane and 100 mL of 1 N NaOH was stirred at rt for 30 min. Di-t-butyldicarbonate (7.6 g, 34.8 mmol) was added and the resulting mixture was stirred at for 30 min. The solids were filtered and the filtrate was partitioned between ether and 1 N HCl. The organic layer was dried and concentrated. Flash chromatography on a Biotage 75S using 4:1 v/v heptane/EtOAc+1% HOAc as the eluant afforded 8.5 g of the title compound: ESI-MS 292 (M-BOC+H); HPLC A: 4.68 min; HPLC B: 4.66 min.

Step D: 3-(R)-(t-Butoxycarbonylamido)-5-(4-octylphenyl) pentanal

The title compound was prepared from 2-(R)-(t-butoxycarbonylamido)-4-(4-octylphenyl)butanoic acid (from EXAMPLE 12, Step C) using procedures analogous to those described in EXAMPLE 5, Steps A and B, EXAMPLE 8, Step A and EXAMPLE 2, Step C.

Step E: Diethyl 1-(R or S)-hydroxy-3-(R)-(t-butoxycarbonylamido)-5-(4-octylphenyl)pentylphosphonate (Isomer 1) and Diethyl 1-(S or R)-hydroxy-3-(R)-(t-butoxycarbonylamido)-5-(4-octylphenyl)pentylphosphonate (Isomer)

A solution of 0.19 mL (1.5 mmol) of diethylphosphite in 10 mL of THF at −5° C. was treated with 1.5 mL of sodium bis(trimethylsilyl)amide solution in THF and stirred cold for 30 min. The resulting mixture was treated with a solution of 363 mg (0.93 mmol) of 3-(R)-(t-butoxycarbonylamido)-5-(4-octylphenyl)pentanal (from EXAMPLE 12, Step D) in 4 mL of THF and the resulting mixture was stirred cold for 20 min. The reaction was quenched with 10 mL of sat'd $NH_4Cl$ and partitioned between 50 mL of EtOAc and 20 mL of water. The organic layer was separated and dried. The aqueous layer was extracted with 50 mL of EtOAc. The extract was separated and dried. The organic layers were combined and concentrated. Flash chromatography on a Biotage 40 M cartridge using 3:1 v/v $CH_2Cl_2$/acetonitrile (1 L), then 1:1 $CH_2Cl_2$/acetonitrile (2 L) as the eluant afforded 180 mg (35%) of Isomer 1 and 88 mg (17%) of Isomer 2. For Isomer 1: $^1$H NMR (500 Mhz) δ 0.88 (t, J=7.0, 3H), 1.22-1.38 (12H), 1.35 (t, J=7.0, 6H), 1.45 (s, 9H), 1.56-1.60 (m, 2H), 1.62-1.70 (m, 1H), 1.71-1.78 (m, 2H), 1.79-1.86 (m, 2H), 1.90-1.97 (m, 2H), 2.56 (t, J=7.5, 2H), 1.60-1.73 (m, 2H), 3.80-3.90 (m, 1H), 3.95 (dt, J=5.0, 12.0, 1H), 4.15-4.23 (4H), 4.42-4.48 (2H), 7.05-7.10 (4H). For Isomer 2: $^1$H NMR (500 Mhz) δ 0.88 (t, J=7.0, 3H), 1.26-1.38 (12H), 1.33 (t, J=7.5, 6H), 1.45 (s, 9H), 1.55-1.60 (2H), 1.68-1.78 (m, 2H), 1.84-1.89 (m, 2H), 2.00-2.08 (m, 1H), 2.56 (t, J=7.5, 2H), 2.58-2.70 (2H), 3.40 (br s, 1H), 3.76 (br s, 1H), 3.98-4.02 (m, 1H), 4.13-4.20 (4H), 4.66 (d, J=8.0, 1H), 7.10 (app s, 4H).

Step F: 1-(R or S)-Hydroxy-3-(R)-amino-5-(4-octylphenyl)pentylphosphonic acid

The title compound was prepared from diethyl 1-(R or S)-hydroxy-3-(R)-(t-butoxycarbonylamido)-5-(4-octylphenyl)pentylphosphonate (Isomer 1) using a procedure analogous to that described in EXAMPLE 3, Step B: HPLC B 2.88 min; ESI-MS 372 (M+H).

Example 13

1-(S or R)-Hydroxy-3-(R)-amino-5-(4-octylphenyl)pentylphosphonic acid

The title compound was prepared from diethyl 1-(S or R)-hydroxy-3-(R)-(t-butoxycarbonylamido)-5-(4-octylphenyl)pentylphosphonate (Isomer 2, from EXAMPLE 12, Step E) using a procedure analogous to that described in EXAMPLE 3, Step B: HPLC B: 2.90 min; ESI-MS 372 (M+H).

Example 14

1-(S or R)-Hydroxy-3-(S)-amino-5-(4-octylphenyl)pentylphosphonic acid

The title compound was prepared from 3-(S)-(t-butoxycarbonylamido)-5-(4-octylphenyl)pentanal using procedures analogous to those described in EXAMPLE 12, Steps E and F: HPLC B: 2.83 min; ESI-MS 372 (M+H).

Example 15

1-(R or S)-Hydroxy-3-(S)-amino-5-(4-octylphenyl)pentylphosphonic acid

The title compound was prepared from 3-(S)-(t-butoxycarbonylamido)-5-(4-octylphenyl)pentanal using procedures analogous to those described in EXAMPLE 12, Step E and EXAMPLE 13: HPLC B: 2.90 min; ESI-MS 372 (M+H).

Examples 16-19

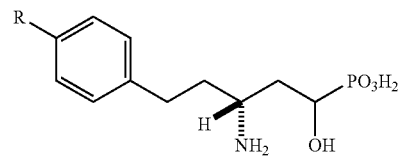

The following compounds were prepared using procedures analogous to those described in EXAMPLE 12 substituting the appropriate arene for 4-octylbenzene in Step A.

| EXAMPLE | R | HPLC B | MS |
| --- | --- | --- | --- |
| 16 | $CH_3(CH_2)_6O-$ | 2.53 | 374 |
| 17 | $Ph(CH_2)_3-$ | 2.37 | 378 |
| 18 | $Ph(CH_2)_4-$ | 2.59 | 392 |
| 19 | $Ph(CH_2)_5-$ | 2.74 | 406 |

Example 20

(+/−)-2-(2-Amino4-(4-octylphenyl)butylthio)imidazole

Step A: (+/−)-1-Iodo-2-(t-butoxycarbonylamido)-4-(4-octylphenyl)butane

The title compound was prepared from (+/−)-2-(t-butoxycarbonylamido)-4-(4-octylphenyl)butanol (from EXAMPLE 2, Step B) using a procedure analogous to that described in EXAMPLE 8, Step B: $^1$H NMR (500 Mhz) δ 0.88 (t, J=7.0, 3H), 1.26-1.30 (12H), 1.54-1.61 (4H), 1.79-1.95 (4H), 2.56 (t, J=7.8, 2H), 3.31-3.46 (3H), 7.07-7.11 (4H).

Step B: (+/−)-2-(2-t-Butoxycarbonylamido-4-(4-octylphenyl)butylthio)imidazole

A mixture of 210 mg (0.43 mmol) of (+/−)-1-iodo-2-(t-butoxycarbonylamido)-4-(4-octylphenyl)butane (from EXAMPLE 20, Step A), 51 mg (0.51 mmol) of 2-mercaptoimidazole and 0.97 mL of DIEA in 4 mL of $CH_3CN$ was heated at reflux for 3 h. The mixture was cooled and partitioned between 50 mL of ether and 25 mL of water. The organic layer was washed with 25 mL of sat'd NaCl, dried and concentrated. Chromatography on a Biotage 40S cartridge using 2:1 v/v hexanes/EtOAc afforded 150 mg of impure title compound: HPLC B: 3.60 min; ESI-MS 360 (M-BOC+H).

Step C: (+/−)-2-(2-Amino-4-(4-octylphenyl)butylthio)imidazole

A solution of 150 mg of impure (+/−)-2-(2-t-butoxycarbonylamido-4-(4-octylphenyl)butylthio) imidazole (from EXAMPLE 20, Step B) in 4 mL of sat'd HCl in MeOH was stirred at rt for 2 h. The solution was concentrated. Chromatography on a Biotage 40S cartridge using 20:1:0.1 v/v/v $CH_2Cl_2$/MeOH/$NH_4OH$ as the eluant afforded 113 mg of the title compound: $^1$H NMR ($CD_3OD$, 500 Mhz) δ 0.89 (t, J=7.0, 3H), 1.26-1.38 (12H); 1.56-1.58 (m, 2H), 1.95-2.08 (m, 2H), 2.55 (t, J=7.7, 2H), 2.60-2.70 (m, 2H), 3.15-3.19 (m, 1H), 3.34-3.39 (m, 2H), 7.05-7;12 (6H); HPLC B: 2.53 min; ESI-MS 360 (M+H).

Example 21

(+/−)-3-(2-Amino-4-(4-octylphenyl)butylthio)-1,2,4-triazole

The title compound was prepared from (+/−)-2-(t-butoxycarbonylamido)-4-(4-octylphenyl)butanol (from EXAMPLE 2, Step B) using a procedure analogous to that described in EXAMPLE 20 substituting 3-mercapto-1,2,4-triazole for 2-mercaptoimidazole in Step B: $^1$H NMR (500 Mhz) δ 0.87 (t, J=7.0, 3H), 1.26-1.29 (12H), 1.54-1.60 (m, 2H), 1.80-1.98 (m, 2H), 2.55 (t, J=7.8, 2H), 2.62-2.73 (m, 2H), 3.04-3.09 (m, 1H), 3.22-3.32 (m, 2H), 5.88 (br s, 2H), 7.05-7.12 (4H), 8.00 (s, 1H); HPLC B: 2.96 min; ESI-MS 361 (M+H).

Example 22

(+/−)-1-H-5-(2-Amino-4-(4-octylphenyl)butylthio)-1,2,3-triazole

The title compound was prepared from (+/−)-2-(t-butoxycarbonylamido)-4-(4-octylphenyl)butanol (from EXAMPLE 2, Step B) using a procedure analogous to that described in EXAMPLE 20 substituting 1-H-5-mercapto-1,2,3-triazole for 2-mercaptoimidazole in Step B: $^1$H NMR (500 Mhz) δ 0.87 (t, J=7.0, 3H), 1.22-1.26 (12H), 1.55-1.62 (m, 2H), 1.75-1.84 (m, 1H), 1.86-1.94 (m, 1H), 2.55 (t, J=7.8, 2H), 2.58-2.66 (m, 1H), 2.67-2.73 (m, 1H), 2,84-2.89 *m, 1H), 3.06-3.16 (m, 1H), 5.09 (br s, 2H), 7.05-7.09 (4H), 7.56 (s, 1H); HPLC B: 2.93 min; ESI-MS 361 (M+H).

Example 23

(+/−)-3-(2-Amino4-(4-octylphenyl)butylsulfonyl)-1,2,4-triazole

Step A: (+/−)-3-(2-t-Butoxycarbonylamido-4-(4-octylphenyl)butylsulfonyl)-1,2,4-triazole A solution of 81 mg (0.18 mmol) of (+/−)-3-(2-t-butoxycarbonylamido-4-(4-octylphenyl)butylthio)-1,2,4-triazole (from EXAMPLE 21.) in 4 mL of $CH_2Cl_2$ at 0° C. was treated with 67 mg (0.39 mmol) of 3-chloroperoxybenzoic acid. The resulting mixture was warmed to rt and stirred for 1.5 h. The reaction mixture was partitioned between 50 mL of EtOAc and 25 mL of 1 N NaOH and the layers were separated. The organic layer was washed with 25 mL of sat'd NaCl, dried and concentrated. Chromatography on a Biotage 40S cartridge using 3:2 v/v EtOAc/hexanes+1% HOAc as the eluant afforded 82% of the title compound: $^1$H NMR (500 Mhz) δ 0.87 (t, J=7.0, 3H), 1.21-1.34 (12H), 1.38 (s, 9H), 1.54-1.59 (m, 2H), 1.96-2.10 (m, 2H), 2.53-2.69 (4H), 3.49-3.57 (m, 1H), 3.69-3.80 (m, 1H), 4.07-4.12 (m, 1H), 4.82-4.92 (m, 1H), 7.01-7.18 (4H), 8.50 (s, 1H); HPLC B: 4.56 min.

Step B: (+/−)-3-(2-Amino-4-(4-octylphenyl)butylsulfonyl)-1,2,4-triazole

The title compound was prepared from (+/−)-3-(2-t-butoxycarbonylamido-4-(4-octylphenyl)butylsulfonyl)-1,2,4-triazole (from EXAMPLE 23, Step A) using a procedure analogous to that described in EXAMPLE 20, Step C: HPLC B: 2.80 min; ESI-MS 393 (M+H).

Example 24

(+/−)-3-(2-Amino-4-(4-octylphenyl)butylsulfonyl)-1.2,4-triazole

The title compound was prepared from (+/−)-1-H-5-(2-t-butoxycarbonylamido-4-(4-octylphenyl)butylthio)-1,2,3-triazole (from EXAMPLE 22) using procedures analogs to those described in EXAMPLE 23: HPLC B: 3.12 min; ESI-MS 393 (M+H).

Example 25

1-(R or S)-Hydroxy-3-(R)-amino-5-(3-methoxy-5-methyl-4-octyloxyphenyl) pentylphosohonic acid Step A: 1-Bromo-3-methoxy-5-methyl-4-octyloxybenzene A solution of 5.89 g (27 mmol) of 1-bromo-4-hydroxy-3-methoxy-5-methylbenzene (Syn. Lett. 1997, 1351-1352) in 100 mL of acetonitrile was treated with 5.33 g (38.5 mmol) of powdered $K_2CO_3$ and 5.75 mL (31.8 mmol) of 1-iodooctane. After stirring at 85° C. for 19 h, the reaction was cooled and concentrated. The residue was dissolved in 100 mL of $H_2O$ and extracted with 100 mL of $Et_2O$. After separating phases, the organic layer was washed with 100 mL of 10% $Na_2S_2O_3$, dried over $MgSO_4$ and concentrated. The residue was purified on a Biotage 40L column using a gradient of hexane, 99/1 v/v hexane/EtOAc and 98/2 v/v hexane/EtOAc to afford 0.43 g of the title compound as a colorless oil. Several mixed column fractions were rechromatographed to yield an additional 703 mg of the title compound. $R_F$: 0.63 (19/1 v/v hexane/EtOAc); $^1$H-NMR (500 MHz) δ 0.93 (t, J=6.8, 3H), 1.33-1.39 (m, 8H), 1.46-1.52 (m, 2H), 1.75-1.81 (m, 2H), 2.27 (s, 3H), 3.85 (s, 3H), 3.91 (t, J=6.6, 2H), 6.90 (d, J=2.3, 11H), 6.95 (d, J=2.3, 11H).

Step B: 3-tert-Butoxycarbonyl-2,2-dimethyl-4-(R)-[2-(3-methoxy-5-methyl-4-octyloxyphen)ethyl]oxazolidine According to the method of Sabat and Johnson (Org. Lett. 2000, 2, 1089-1092), a solution of 312 mg (1.3 mmol) of 3-tert-butoxycarbonyl-2,2-dimethyl-4-(R)-vinyloxazolidine (Synthesis 1994, 1463-1466) in 6 mL of toluene was treated with 5.2 mL (2.6 mmol) of 0.5M 9-borabicylo[3.3.1]nonane (9-BBN) in THF. After stirring at 80° C. for 40 min under argon, the reaction was cooled and treated with 1.6 mL (5.1 mmol) of 3.2N NaOH, 32 mg (0.035 mmol) of tris(dibenzylideneacetone)dipalladium(0), 70 mg (0.26 mmol) of triphenylphosphine, a solution of 430 mg (1.3 mmol) of 1-bromo-3-methoxy-5-methyl-4-octyloxybenzene (from Step A) in 2 mL of toluene and 241 mg (0.65 mmol) of tetrabutylammonium iodide. After stirring at 90° C. for 16 hours, the reaction was cooled, poured into 50 mL of $H_2O$ and extracted with 2×50 mL of $Et_2O$. The combined organic layers were dried over $MgSO_4$ and concentrated. The residue was purified on a Biotage 40M column using a gradient of 92.5/7.5 v/v hexane/Et$_2$O and 9/1 v/v hexane/Et$_2$O to afford 598 mg of the title compound as a gold oil. R$_F$: 0.16 (9/1 v/v hexane/Et$_2$O); $^1$H-NMR (500 MHz, rotamers) δ 0.91 (t, J=6.9, 3H), 1.19-1.97 (m, 29H), 2.24 (s, 3H), 2.37-2.57 (m, 2H), 3.80-3.98 (m, 7H), 4.24,4.39 (2 br m, 1H), 6.55-6.61 (m, 2H).

Step C: 2-(R)-[N-(tert-Butoxycarbonyl)amino]-4-(3-methoxy-5-methyl-4-octyloxyphenyl)-1-butanol A solution of 598 mg (1.2 mmol) of 3-tert-butoxycarbonyl-2,2-dimethyl-4-(R)-[2-(3-methoxy-5-methyl-4-octyloxyphen)ethyl]oxazolidine (from Step B) in 6 mL of MeOH was treated with 0.20 mL (2.5 mmol) of pyridine and 0.47 g (2.5 mmol) of para-toluenesulfonic acid. After refluxing for 3 h, the reaction was concentrated and partitioned between 50 mL of H$_2$O and 50 mL of Et$_2$O. After separating phases, the aqueous layer was extracted with 50 mL of Et$_2$O. The combined organics were washed with 100 mL 1N NaHCO$_3$, 100 mL of H$_2$O and 100 mL of brine. The organic phases were dried over MgSO$_4$ and concentrated. The residue was purified on a Biotage 40M column using a gradient of 3/1 v/v hexane/EtOAc and 7/3 v/v hexane/EtOAc to afford 339 mg of the title compound as a colorless oil. R$_F$: 0.19 (7/3 v/v hexane/EtOAc); $^1$H-NMR (500 MHz) δ 0.91 (t, J=6.9, 3H), 1.27-1.46 (m, 7H), 1.48 (s, 9H), 1.72-1.87 (m, 6H), 1.99 (br m, 1H), 2.24 (s, 3H), 2.56-2.68 (m, 2H), 3.58-3.71 (m, 4H), 3.83 (s, 3H), 3.89 (t, J=6.7, 2H), 4.70 (br m, 1H), 6.59 (s, 1H), 6.60 (s, 1H).

Step D: 3-(R)-[N-(tert-Butoxycarbonyl)amino]-5-(3-methoxy-5-methyl-4-octyloxyphenyl)-pentanenitrile A solution of 510 mg (1.1 mmol) of 2-(R)-[N-(tert-butoxycarbonyl)amino]-4-(3-methoxy-5-methyl-4-octyloxyphenyl)-1-butanol (from Step C) in 8 mL of CH$_2$Cl$_2$ at 0° C. was treated simultaneously with 0.14 mL (1.8 mmol) of methanesulfonyl chloride and 0.25 mL (1.8 mmol) of triethylamine. After 30 min at 0° C., the reaction was warmed to room temperature, poured into 100 mL of brine and extracted with 100 mL of Et$_2$O. After separating phases, the organic layer was washed with 100 mL of brine, 100 mL of 0.5 N HCl, 100 mL of brine, 100 mL of 1 N NaHCO$_3$ and 100 mL of brine. The organics were dried over MgSO$_4$ and concentrated. The crude mesylate was taken on without further purification.

A solution of the mesylate in 6 mL of DMF was treated with 0.14 g (2.8 mmol) of powdered NaCN. After stirring 43 h at room temperature, the reaction was poured into 100 mL of Et$_2$O and washed with 2×100 mL of H$_2$O. The organics were dried over MgSO$_4$ and concentrated. The residue was purified on a Biotage 40M column eluting with 17/3 v/v hexane/EtOAc to afford 151 mg of the title compound as a colorless oil. R$_F$: 0.36 (4/1 v/v hexane/EtOAc); $^1$H-NMR (500 MHz) δ 0.91 (t, J=7.0, 3H), 1.28-1.51 (m, 18H), 1.72-1.80 (m, 2H), 1.90-1.95 (m, 2H), 2.25 (s, 3H), 2.51-2.80 (m, 4H), 3.84 (s, 3H), 3.85-3.88 (m, 2 H), 3.89 (t, J=6.8, 2H), 4.69 (d, J=7.7, 1H), 6.56-6.58 (m, 2H).

Step E: 3-(R)-[N-(tert-Butoxycarbonyl)amino]-5-(3-methoxy-5-methyl-4-octyloxyphenyl)-pentanal A solution of 220 mg (0.49 mmol) of 3-(R)-[N-(tert-butoxycarbonyl)amino]-5-(3-methoxy-5-methyl-4-octyloxyphenyl)-pentanenitrile (from Step D) in 10 mL of Et$_2$O at −60° C. was treated with 2.0 mL (2.0 mmol) of 1M Dibal in toluene over 4 h via a syring pump. After stirring for 1 h additional at −60° C., the reaction was quenched with MeOH and warmed to room temperature. The mixture was poured into 50 mL of saturated NH$_4$Cl (pH adjusted to 3 with 2 N HCl). After separating phases, the aqueous layer was extracted with 2×50 mL of EtOAc (aqueous pH maintained at 3 to avoid an emulsion). The combined organics were dried over Na$_2$SO$_4$ and concentrated. The residue was purified by flash chromatography eluting with 4/1 v/v hexane/EtOAc to afford 95 mg of the title compound as a colorless film. R$_F$: 0.20 (4/1 v/v hexane/EtOAc); $^1$H-NMR (500 MHz) δ 0.91 (t, J=6.9, 3H), 1.27-1.86 (m, 23H), 2.25 (s, 3H), 2.54-2.70 (m, 4H), 3.84 (s, 3H), 3.89 (t, J=6.8, 2H), 4.08 (m, 1H), 4.72 (m, 1H), 6.57-6.58 (m, 2H), 9.77 (s, 1H).

Step F: 1-(R or S)-Hydroxy-3-(R)-amino-5-(3-methoxy-5-methyl-4-octyloxyphenyl)pentylphosphonic acid, diethyl ester A solution of 0.041 mL (0.3 mmol) of diethyl phosphite in 2 mL of THF at 0° C. was treated with 0.32 mL (0.32 mmol) of 1 M sodium bis(trimethyl-silyl)amide in THF. After 20 min, a solution of 92 mg (2 mmol) of 3-(R)-[N-(tert-butoxycarbonyl)amino]-5-(3-methoxy-5-methyl-4-octyloxyphenyl)-pentanal (from Step E) in 3 mL of THF was added. After stirring at 0° C. for 1 h, the reaction was poured into 25 mL of saturated NH$_4$Cl and extracted with 2×25 mL of Et$_2$O. The combined organics were dried over MgSO$_4$ and concentrated. The residue was purified by flash chromatography eluting with a gradient of 3/1 v/v CH$_2$Cl$_2$/CH$_3$CN and 1/1 v/v CH$_2$Cl2/CH$_3$CN to afford 54 mg of the major diastereomer and 12 mg of the minor diastereomer both as colorless films. Major Diastereomer: R$_F$: 0.74 (1/1 v/v CH$_2$Cl$_2$/CH$_3$CN); $^1$H-NMR (500 MHz) δ 0.91 (t, J=6.9, 3H), 1.31-1.50 (m, 24H), 1.65-1.98 (m, 7H), 2.24 (s, 3H), 2.56-2.69 (m, 2H), 3.83 (s, 3H), 3.86-3.99 (m, 4H), 4.174.25 (m, 4H), 4.48 (d, J=9.1, 1H), 6.54-6.56 (m, 2H); Minor Diastereomer: R$_F$: 0.65 (1/1 v/v CH$_2$Cl$_2$/CH$_3$CN); $^1$H-NMR (500 MHz) δ 0.90 (t, J=7.0, 3H), 1.30-1.50 (m, 24H),;1.71-1.91 (m, 6H), 2.03 (m, 1H), 2.23 (s, 3H), 2.53-2.66 (m, 2H), 3.02 (br m, 1H), 3.78-3.90 (m, 6H), 4.02 (m, 1H), 4.15-4.22 (m, 4H), 4.78 (m, 1H), 6.54-6.57 (m, 2H).

Step G: 1-(R or S)-Hydroxy-3-(R)-amino-5-(3-methoxy-5-methyl-4-octyloxyphenyl)pentylphosphonic acid A solution of 54 mg (0.09 mmol) of 1-(R or S)-hydroxy-3-(R)-amino-5-(3-methoxy-5-methyl-4-octyloxyphenyl) pentylphosphonic acid, diethyl ester (major diastereomer from Step F) and 0.06 mL (0.45 mmol) of bromotrimethylsilane in 2 ml of CH$_3$CN was stirred at 75° C. for 1 h. Some starting material was still present, so an additional 0.012 mL (0.09 mmol) of bromotrimethylsilane was added. After 30 min at 75° C., the reaction was quenched with MeOH and concentrated. The residue was concentrated from MeOH (3×), dissolved in 2 mL of CH$_3$CN and placed in the freezer for 2.5 days. The supernatant was removed to afford a colorless film (assumed quantitative). ESI-MS 432.2 (M+H); LC-1: 2.90 min.

Example 26

1-(R or S)-Hydroxy-3-(R)-amino-5-(4-heptylphenyl) pentylphosphonic acid

The title compound was prepared using procedures analogous to those described in Example 25 substituting trifluoromethanesulfonic acid, 4-heptylphenyl ester for 1-bromo-3-methoxy-5-methyl-4-octyloxybenzene in Step B. ESI-MS 358.4 (M+H); LC-1: 2.72 min.

Example 27

(±)-3-(Amino)pentadecylphosphonic acid

Step A: (±)-Diethyl 3-(carboethoxy)pentadecylphosphonate

A solution of triethyl 4-phosphonobutyrate (1.00 g, 3.96 mmol) in 1 mL of THF was added to potassium bis(trimethylsilyl)amide (0.5 M in THF, 8.70 ml, 4.36 mmol) at −78° C. After stirring for 1 h at −78° C., 1-iodododecane (1.2 mL, 4.75 mmol) was added dropwise. The reaction was removed from the bath, warmed to rt and stirred for 2 h. The reaction was diluted with ethyl acetate (50 ml), washed with 2 N HCl (50 mL), sat'd NaCl (50 mL), dried and concentrated. Flash chromatography using 3:1 v/v hexane/acetone afforded 610 mg of the title compound: ESI-MS 421.3 (M+H).

Step B: (±)-Diethyl 3-(carboxy)pentadecylphosphonate

A solution 0.61 g (1.44 mmol) of (±)-diethyl 3-(carboethoxy)pentadecyl phosphonate (from Example 27, Step A) in 10 mL of MeOH was treated with 4.3 mL of 1 N NaOH. The resulting mixture was stirred at rt for 2 h then heated to 50° C. for 16 h. The reaction was diluted with 75 mL of EtOAc, washed with 50 mL of 2 N HCl, 50 mL of sat'd NaCl, dried and concentrated to give 0.62 g of the title compound: ESI-MS 393.1 (M+H).

Step C: (±)-Diethyl 3-(benzyloxycarbonylamino)pentadecylphosphonate

A solution of 0.62 g (1.6 mmol) of (±)-diethyl 3-(carboxy)pentadecylphosphonate (from Example 27, Step B) in 5 mL of THF at 0° C. was treated with 0.27 mL (1.9 mmol) of TEA and 0.23 mL (1.9 mmol) of methyl chloroformate. The resulting mixture was stirred cold for 30 min, then treated with a solution of 0.51 g (7.9 mmol) of sodium azide in 3 mL of water. The resulting mixture was stirred for 2 h at 0° C. The reaction was diluted with 50 mL of EtOAc, washed with 50 mL of 2 N HCl, 50 mL of sat'd NaCl, dried and concentrated. The residue was dissolved in 5 mL of toluene, benzyl alcohol (0.33 mL, 3.2 mmol) was added and the solution was heated to 85° C. for 3 h. The reaction was cooled and directly purified by silica gel chromatography using 7:3 v/v hexane/acetone as the eluant to afford 0.45 g of the title compound: ESI-MS 498.3 (M+H).

Step D: (±)-3-(Amino)pentadecylphosphonic acid

A solution of 100 mg (0.2 mmol) of (±)-diethyl 3-(benzyloxycarbonylamino)pentadecylphosphate (from Example 27, Step C) in 1 mL of $CH_2Cl_2$ was treated with 0.11 mL (0.8 mmol) of iodotrimethylsilane then stirred at rt for 1 h. The reaction was quenched with 1 mL of methanol, stirred at rt for 15 min then concentrated. The resulting oil was dissolved in 0.5 mL of EtOAc, diluted with 5 mL of hexanes and. sonicated for 1 min. The suspension was filtered and dried to give 68 mg of the title compound: $^1$H NMR (500 MHz) δ 3.22-3.30 (m, 1H), 1.76-2.01 (m, 4H), 1.56-1.70 (m, 2H), 1.26-1.46 (m, 20H), 0.89 (t, J=6.9 Hz, 3H); ESI-MS 308.2 (M+H).

Examples 28-37

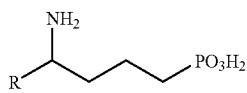

Examples 28-37 were prepared using procedures analogous to those described in Example 27 substituting the appropriate alkyl halide for 1-iodododecane in Step A. In cases were sonication in Step D did not yield pure material, further purification was carried out using HPLC C.

| EX-AMPLE | R | HPLC B (min) | ESI-MS |
|---|---|---|---|
| 28 | $CH_3—(CH_2)_9—$ | 2.32 | 280 |
| 29 | $CH_3—(CH_2)_{10}—$ | 2.48 | 294 |
| 30 | $CH_3—(CH_2)_{12}—$ | 3.01 | 322 |
| 31 | $CH_3—(CH_2)_{13}—$ | 3.1 | 336 |
| 32 | $CH_3—(CH_2)_{14}—$ | 3.65 | 364 |
| 33 | $CH_3—(CH_2)_{16}—$ | 3.92 | 378 |
| 34 | $CH_3—(CH_2)_{17}—$ | 4.16 | 392 |
| 35 | 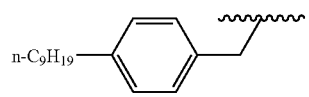 | 2.96 | 356 |
| 36 |  | 2.88 | 356 |
| 37 | 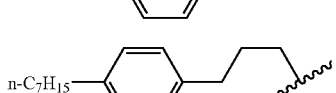 | 2.93 | 356 |

Biological Activity

The $S1P_1$/Edg1, $S1P_3$/Edg3, $S1P_2$/Edg5, $S1P_4$/Edg6 or $S1P_5$/Edg8 activity of the compounds of the present invention can be evaluated using the following assays:

Ligand Binding to Edg/S1P Receptors Assay $^{33}$P-sphingosine-1-phosphate was synthesized enzymatically from γ$^{33}$P-ATP and sphingosine using a crude yeast extract with sphingosine kinase activity in a reaction mix containing 50 mM $KH_2PO_4$, 1 mM mercaptoethanol, 1 mM $Na_3VO_4$, 25 mM KF, 2 mM semicarbazide, 1 mM $Na_2EDTA$, 5 mM $MgCl_2$, 50 mM sphingosine, 0.1% TritonX-114, and 1 mCi γ$^{33}$P-ATP (NEN; specific activity 3000 Ci/mmol). Reaction products were extracted with butanol and $^{33}$P-sphingosine-1-phosphate was purified by HPLC.

Cells expressing EDG/S1P receptors were harvested with enzyme-free dissociation solution (Specialty Media, Lavallette, N.J.). They were washed once in cold PBS and suspended in binding assay buffer consisting of 50 mM HEPES-Na, pH 7.5, 5mM $MgCl_2$, 1 mM $CaCl_2$, and 0.5% fatty acid-free BSA. $^{33}$P-sphingosine-1-phosphate was sonicated with 0.1 nM sphingosine-1-phosphate in binding assay buffer; 100 µl of the ligand mixture was added to 100 µl cells ($1\times10^6$ cells/ml) in a 96 well microtiter dish. Binding was performed for 60 min at room temperature with gentle mixing. Cells were then collected onto GF/B filter plates with a Packard Filtermate Universal Harvester. After drying the filter plates for 30 min, 40 µl of Microscint 20 was added to each well and binding was measured on a Wallac Microbeta Scintillation Counter. Non-specific binding was defined as the amount of radioactivity remaining in the presence of 0.5 µM cold sphingosine-1-phosphate.

Alternatively, ligand binding assays were performed on membranes prepared from cells expressing Edg/S1P receptors. Cells were harvested with enzyme-free dissociation solution and washed once in cold PBS. Cells were disrupted by homogenization in ice cold 20 mM HEPES pH 7.4, 10 mM EDTA using a Kinematica polytron (setting 5, for 10 seconds). Homogenates were centrifuged at 48,000×g for 15 min at 4° C. and the pellet was suspended in 20 mM HEPES pH 7.4, 0.1 mM EDTA. Following a second centrifugation, the final pellet was suspended in 20 mM HEPES pH 7.4, 100 mM NaCl, 10 mM MgCl$_2$. Ligand binding assays were performed as described above, using 0.5 to 2 µg of membrane protein.

Agonists and antagonists of Edg/S1P receptors can be identified in the $^{33}$P-sphingosine-1-phosphate binding assay. Compounds diluted in DMSO, methanol, or other solvent, were mixed with probe containing $^{33}$P-sphingosine-1-phosphate and binding assay buffer in microtiter dishes. Membranes prepared from cells expressing Edg/S1P receptors were added, and binding to $^{33}$P-sphingosine-1-phosphate was performed as described. Determination of the amount of binding in the presence of varying concentrations of compound and analysis of the data by non-linear regression software such as MRLCalc (Merck Research Laboratories) or PRISM (GraphPad Software) was used to measure the affinity of compounds for the receptor. Selectivity of compounds for Edg/S1P receptors was determined by measuring the level of $^{33}$P-sphingosine-1-phosphate binding in the presence of the compound using membranes prepared from cells transfected with each respective receptor (S1P$_1$/Edg1, S1P$_3$/Edg3, S1P$_2$/Edg5, S1P$_4$/Edg6, S1P$_5$/Edg8).

$^{35}$S-GTPγS Binding Assay

Functional coupling of S1P/Edg receptors to G proteins was measured in a $^{35}$S-GTPγS binding assay. Membranes prepared as described in the Ligand Binding to Edg/S1P Receptors Assay (1-10 µg of membrane protein) were incubated in a 200 µl volume containing 20 mM HEPES pH 7.4, 100 mM NaCl, 10 mM MgCl$_2$, 5 µM GDP, 0.1% fatty acid-free BSA (Sigma, catalog A8806), various concentrations of sphingosine-1-phosphate, and 125 pM $^{35}$S-GTPγS (NEN; specific activity 1250 Ci/mmol) in 96 well microtiter dishes. Binding was performed for 1 hour at room temperature with gentle mixing, and terminated by harvesting the membranes onto GF/B filter plates with a Packard Filtermate Universal Harvester. After drying the filter plates for 30 min, 40 µl of Microscint 20 was added to each well and binding was measured on a Wallac Microbeta Scintillation Counter.

Agonists and antagonists of S1P/Edg receptors can be discriminated in the $^{35}$S-GTPγS binding assay. Compounds diluted in DMSO, methanol, or other solvent, were added to microtiter dishes to provide final assay concentrations of 0.01 nM to 10 µM. Membranes prepared from cells expressing S1P/Edg receptors were added, and binding to $^{35}$S-GTPγS was performed as described. When assayed in the absence of the natural ligand or other known agonist, compounds that stimulate $^{35}$S-GTPγS binding above the endogenous level were considered agonists, while compounds that inhibit the endogenous level of $^{35}$S-GTPγS binding were considered inverse agonists. Antagonists were detected in a $^{35}$S-GTPγS binding assay in the presence of a sub-maximal level of natural ligand or known S1P/Edg receptor agonist, where the compounds reduced the level of $^{35}$S-GTPγS binding. Determination of the amount of binding in the presence of varying concentrations of compound was used to measure the potency of compounds as agonists, inverse agonists, or antagonists of S1P/Edg receptors. To evaluate agonists, percent stimulation over basal was calculated as binding in the presence of compound divided by binding in the absence of ligand, multiplied by 100. Dose response curves were plotted using a non-linear regression curve fitting program MRLCalc (Merck Research Laboratories), and EC$_{50}$ values were defined to be the concentration of agonist required to give 50% of its own maximal stimulation. Selectivity of compounds for S1P/Edg receptors was determined by measuring the level of $^{35}$S-GTPγS binding in the presence of compound using membranes prepared from cells transfected with each respective receptor.

Intracellular Calcium Flux Assay

Functional coupling of S1P/Edg receptors to G protein associated intracellular calcium mobilization was measured using FLIPR (Fluorescence Imaging Plate Reader, Molecular Devices). Cells expressing S1P/Edg receptors were harvested and washed once with assay buffer (Hanks Buffered Saline Solution (BRL) containing 20 mM HEPES, 0.1% BSA and 710 µg/ml probenicid (Sigma)). Cells were labeled in the same buffer containing 500 nM of the calcium sensitive dye Fluo-4 (Molecular Probes) for 1 hour at 37° C. and 5% CO$_2$. The cells were washed twice with buffer before plating 1.5×10$^5$ per well (90 µl) in 96 well polylysine coated black microtiter dishes. A 96-well ligand plate was prepared by diluting sphingosine-1-phosphate or other agonists into 200 µl of assay buffer to give a concentration that was 2-fold the final test concentration. The ligand plate and the cell plate were loaded into the FLIPR instrument for analysis. Plates were equilibrated to 37° C. The assay was initiated by transferring an equal volume of ligand to the cell plate and the calcium flux was recorded over a 3 min interval. Cellular response was quantitated as area (sum) or maximal peak height (max). Agonists were evaluated in the absence of natural ligand by dilution of compounds into the appropriate solvent and transfer to the Fluo-4 labeled cells. Antagonists were evaluated by pretreating Fluo-4 labeled cells with varying concentrations of compounds for 15 min prior to the initiation of calcium flux by addition of the natural ligand or other S1P/Edg receptor agonist.

Preparation of Cells Expressing S1P/Edg Receptors

Any of a variety of procedures may be used to clone S1P$_1$/Edg1, S1P$_3$/Edg3, S1P$_2$/Edg5, S1P$_4$/Edg6 or S1P$_5$/Edg8. These methods include, but are not limited to, (1) a RACE PCR cloning technique (Frohman, et al., 1988, *Proc. Natl. Acad. Sci. USA* 85: 8998-9002). 5' and/or 3' RACE may be performed to generate a full-length cDNA sequence; (2) direct functional expression of the Edg/S1P cDNA following the construction of an S1P/Edg-containing cDNA library in an appropriate expression vector system; (3) screening an S1P/Edg-containing cDNA library constructed in a bacteriophage or plasmid shuttle vector with a labeled degenerate oligonucleotide probe designed from the amino acid sequence of the S1P/Edg protein; (4) screening an S1P/Edg-containing cDNA library constructed in a bacteriophage or plasmid shuttle vector with a partial cDNA encoding the S1P/Edg protein. This partial cDNA is obtained by the specific PCR amplification of S1P/Edg DNA fragments through the design of degenerate oligonucleotide primers from the amino acid sequence known for other proteins which are related to the S1P/Edg protein; (5) screening an S1P/Edg-containing cDNA library constructed in a bacteriophage or plasmid shuttle vector with a partial cDNA or oligonucleotide with homology to a mammalian S1P/Edg protein. This strategy may also involve using gene-specific oligonucleotide primers for PCR amplification of S1P/Edg cDNA; or (6) designing 5' and 3' gene specific oligonucleotides using the S1P/Edg nucleotide sequence as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding S1P/Edg.

It is readily apparent to those skilled in the art that other types of libraries, as well as libraries constructed from other cell types-or species types, may be useful for isolating an S1P/Edg-encoding DNA or an S1P/Edg homologue. Other types of libraries include, but are not limited to, cDNA libraries derived from other cells.

It is readily apparent to those skilled in the art that suitable cDNA libraries may be prepared from cells or cell lines which have S1P/Edg activity. The selection of cells or cell lines for use in preparing a cDNA library to isolate a cDNA encoding S1P/Edg may be done by first measuring cell-associated S1P/Edg activity using any known assay available for such a purpose.

Preparation of cDNA libraries can be performed by standard techniques well known in the art. Well known cDNA library construction techniques can be found for example, in Sambrook et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

An expression vector containing DNA encoding an S1P/Edg-like protein may be used for expression of S1P/Edg in a recombinant host cell. Such recombinant host cells can be cultured under suitable conditions to produce S1P/Edg or a biologically equivalent form. Expression vectors may include, but are not limited to, cloning vectors, modified cloning vectors, specifically designed plasmids or viruses. Commercially available mammalian expression vectors may be suitable for recombinant S1P/Edg expression.

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells including but not limited to *Drosophila* and silkworm derived cell lines.

The nucleotide sequences for the various S1P/Edg receptors are known in the art. See, for example, the following:

S1P$_1$/Edg1 Human

Hla, T. and T. Maciag 1990 An abundant transcript induced in differentiating human endothelial cells encodes a polypeptide with structural similarities to G-protein coupled receptors. J. Biol Chem. 265: 9308-9313, hereby incorporated by reference in its entirety.

WO91/15583, published on Oct. 17, 1991, hereby incorporated by reference in its entirety.

WO99/46277, published on Sep. 16, 1999, hereby incorporated by reference in its entirety.

S1P$_1$/Edg1 Mouse

WO0059529, published Oct. 12, 2000, hereby incorporated by reference in its entirety.

U.S. Pat. No 6,323,333, granted Nov. 27, 2001, hereby incorporated by reference in its entirety.

S1P$_1$/Edg1 Rat

Lado, D. C., C. S. Browe, A. A. Gaskin, J. M. Borden, and A. J. MacLennan. 1994 Cloning of the rat edg-1 immediate-early gene: expression pattern suggests diverse functions. Gene 149: 331-336, hereby incorporated by reference in its entirety.

U.S. Pat. No. 5,585,476, granted Dec. 17, 1996, hereby incorporated by reference in its entirety.

U.S. Pat. No. 5856,443, granted Jan. 5, 1999, hereby incorporated by reference in its entirety.

S1P$_3$/Edg3 Human

An, S., T. Bleu, W. Huang, O. G. Hallmark, S. R. Coughlin, E. J. Goetzl 1997 Identification of cDNAs encoding two G protein-coupled receptors for lysosphingolipids FEBS Lett. 417: 279-282, hereby incorporated by reference in its entirety.

WO 99/60019, published Nov. 25, 1999, hereby incorporated by reference in its entirety.

U.S. Pat. No. 6,130,067, granted Oct. 10, 2000, hereby incorporated by reference in its entirety.

S1P$_3$/Edg3 Mouse

WO 01/11022, published Feb. 15, 2001, hereby incorporated by reference in its entirety.

S1P$_3$/Edg3 Rat

WO 01/27137, published Apr. 19, 2001, hereby incorporated by reference in its entirety.

S1P$_2$/Edg5 Human

An, S., Y. Zheng, T. Bleu 2000 Sphingosine 1-Phosphate-induced cell proliferation, survival, and related signaling events mediated by G Protein-coupled receptors Edg3 and Edg5. J. Biol. Chem 275: 288-296, hereby incorporated by reference in its entirety.

WO 99/35259, published Jul. 15, 1999, hereby incorporated by reference in its entirety.

WO99/54351, published Oct. 28, 1999, hereby incorporated by reference in its entirety.

WO 00/56135, published Sep. 28, 2000, hereby incorporated by reference in its entirety.

S1P$_2$/Edg5 Mouse

WO 00/60056, published Oct. 12, 2000, hereby incorporated by reference in its entirety.

S1P$_2$/Edg5 Rat

Okazaki, H., N. Ishizaka, T. Sakurai, K. Kurokawa, K. Goto, M. Kumada, Y. Takuwa 1993 Molecular cloning of a novel putative G protein-coupled receptor expressed in the cardiovascular system. Biochem. Biophys. Res. Comm. 190: 1104-1109, hereby incorporated by reference in its entirety.

MacLennan, A. J., C. S. Browe, A. A. Gaskin, D. C. Lado, G. Shaw 1994 Cloning and characterization of a putative G-protein coupled receptor potentially involved in development. Mol. Cell. Neurosci. 5: 201-209, hereby incorporated by reference in its entirety.

U.S. Pat. No. 5,585,476, granted Dec. 17, 1996, hereby incorporated by reference in its entirety.

U.S. Pat. No. 5,856,443, granted Jan. 5, 1999, hereby incorporated by reference in its entirety.

S1P$_4$/Edg6 Human

Graler, M. H., G. Blemhardt, M. Lipp 1998 EDG6, a novel G-protein-coupled receptor related to receptors for bioactive lysophospholipids, is specifically expressed in lymphoid tissue. Genomics 53: 164-169, hereby incorporated by reference in its entirety.

WO 98/48016, published Oct. 29, 1998, hereby incorporated by reference in its entirety.

U.S. Pat. No. 5,912,144, granted Jun. 15, 1999, hereby incorporated by reference in its entirety.

WO 98/50549, published Nov. 12, 1998, hereby incorporated by reference in its entirety.

U.S. Pat. No. 6,060,272, granted May 9, 2000, hereby incorporated by reference in its entirety.

WO 99/35106, published Jul. 15, 1999, hereby incorporated by reference in its entirety.

WO 00/15784, published Mar. 23, 2000, hereby incorporated by reference in its entirety.

WO 00/14233, published Mar. 16, 2000, hereby incorporated by reference in its entirety.

$S1P_4/Edg6$ Mouse

WO 00/15784, published Mar. 23, 2000, hereby incorporated by reference in its entirety.

$S1P_5/Edg8$ Human

Im, D.-S., J. Clemens, T. L. Macdonald, K. R. Lynch 2001 Characterization of the human and mouse sphingosine 1-phosphate receptor, $S1P_5$ (Edg-8): Structure-Activity relationship of sphingosine 1-phosphate receptors. Biochemistry 40: 14053-14060, hereby incorporated by reference in its entirety.

WO 00/11166, published Mar. 2, 2000, hereby incorporated by reference in its entirety.

WO 00/31258, published Jun. 2, 2000, hereby incorporated by reference in its entirety.

WO 01/04139, published Jan. 18, 2001, hereby incorporated by reference in its entirety.

EP 1 090 925, published Apr. 11, 2001, hereby incorporated by reference in its entirety.

$S1P_5/Edg8$ Rat

Im, D.-S., C. E. Heise, N. Ancellin, B. F. O'Dowd, G.-J. Shei, R. P. Heavens, M. R. Rigby, T. Hla, S. Mandala, G. McAllister, S. R. George, K. R. Lynch 2000 Characterization of a novel sphingosine 1-phosphate receptor, Edg-8. J. Biol. Chem. 275: 14281-14286, hereby incorporated by reference in its entirety.

WO 01/05829, published Jan. 25, 2001, hereby incorporated by reference in its entirety.

Measurement of Cardiovascular Effects

The effects of compounds of the present invention on cardiovascular parameters can be evaluated by the following procedure:

Adult male rats (approx. 350 g body weight) were instrumented with femoral arterial and venous catheters for measurement of arterial pressure and intravenous compound administration, respectively. Animals were anesthetized with Nembutal (55 mg/kg, ip). Blood pressure and heart rate were recorded on the Gould Po—Ne-Mah data acquisition system. Heart rate was derived from the arterial pulse wave. Following an acclimation period, a baseline reading was taken (approximately 20 minutes) and the data averaged. Compound was administered intravenously (either bolus injection of approximately 5 seconds or infusion of 15 minutes duration), and data were recorded every 1 minute for 60 minutes post compound administration. Data are calculated as either the peak change in heart rate or mean arterial pressure or are calculated as the area under the curve for changes in heart rate or blood pressure versus time. Data are expressed as mean ± SEM. A one-tailed Student's paired t-test is used for statistical comparison to baseline values and considered significant at p<0.05.

The S1P effects on the rat cardiovascular system are described in Sugiyama, A., N. N. Aye, Y. Yatomi, Y. Ozaki, K. Hashimoto 2000 Effects of Sphingosine-1-Phosphate, a naturally occurring biologically active lysophospholipid, on the rat cardiovascular system. Jpn. J. Pharmacol. 82: 338-342, hereby incorporated by reference in its entirety.

Measurement of Mouse Acute Toxicity

A single mouse is dosed intravenously (tail vein) with 0.1 ml of test compound dissolved in a non-toxic vehicle and is observed for signs of toxicity. Severe signs may include death, seizure, paralysis or unconciousness. Milder signs are also noted and may include ataxia, labored breathing, ruffling or reduced activity relative to normal. Upon noting signs, the dosing solution is diluted in the same vehicle. The diluted dose is administered in the same fashion to a second mouse and is likewise observed for signs. The process is repeated until a dose is reached that produces no signs. This is considered the estimated no-effect level. An additional mouse is dosed at this level to confirm the absence of signs.

Assessment of Lymphopenia

Compounds are administered as described in Measurement of Mouse Acute Toxicity and lymphopenia is assessed in mice at three hours post dose as follows. After rendering a mouse unconscious by $CO_2$ to effect, the chest is opened, 0.5 ml of blood is withdrawn via direct cardiac puncture, blood is immediately stabilized with EDTA and hematology is evaluated using a clinical hematology autoanalyzer calibrated for performing murine differential counts (H2000, CARESIDE, Culver City Calif.). Reduction in lymphocytes by test treatment is established by comparison of hematological parameters of three mice versus three vehicle treated mice. The dose used for this evaluation is determined by tolerability using a modification of the dilution method above. For this purpose, no-effect is desirable, mild effects are acceptable and severely toxic doses are serially diluted to levels that produce only mild effects.

What is claimed is:

1. A compound represented by Formula I:

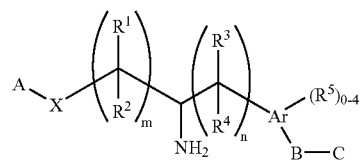

or a pharmaceutically acceptable salt or hydrate thereof, wherein:

Ar is phenyl;

m =1,2,3, or 4;

n=1, 2, 3, or 4;

X is a bond, O, NH or $S(O)_k$, wherein k is 0, 1 or 2;

A is selected from the group consisting of: —$CO_2H$, —$PO_3H_2$, —$PO_2H_2$, —$SO_3H$, —$SO_2CH_3$—$PO(R^8)$OH,

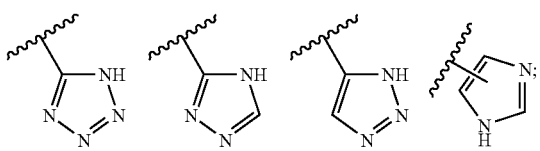

each $R^1$ is independently selected from the group consisting of: hydrogen, hydroxy, and $C_{1-4}$alkyl, wherein said $C_{1-4}$alkyl, is optionally substituted from one up to the maximum number of substitutable positions with halo, or when m is 2, 3, or 4, two $R^1$ groups on adjacent carbon atoms may be joined together to form a double bond;

each $R^3$ is independently selected from the group consisting of: hydrogen, hydroxy, and $C_{1-4}$alkyl, wherein said $C_{1-4}$alkyl, is optionally substituted from one up to the maximum number of substitutable positions with halo, or when n is 2, 3, or 4, two $R^3$ groups on adjacent carbon atoms may be joined together to form a double bond;

$R^2$ and $R^4$ are each independently selected from the group consisting of: hydrogen, hydroxy, and $C_{1-4}$alkyl, wherein said $C_{1-4}$alkyl, is optionally substituted from one up to the maximum number of substitutable positions with halo;

or $R^1$ and $R^2$ or $R^3$ and $R^4$ residing on the same carbon atom may optionally be joined together to form a carbonyl group, each $R^5$ is independently selected from the group consisting of: halo, aryl, $C_{1-6}$alkyl, $C_{3-6}$cycloalkyl, $C_{1-6}$alkoxy, $C_{1-6}$alkylthio and $C_{3-6}$cycloalkoxy, said $C_{1-6}$alkyl, $C_{3-6}$cycloalkyl, $C_{1-6}$alkoxy, $C_{1-6}$alkylthio and $C_{3-6}$cycloalkoxy optionally substituted from one up to the maximum number of substitutable positions with halo, $R^8$ is selected from the group consisting of: $C_{1-4}$alkyl and aryl, wherein said $C_{1-4}$alkyl is optionally substituted with 1-3 halo groups and aryl is optionally substituted with 1-5 substituents independently selected from the group consisting of: halo, $C_{1-6}$alkyl, $C_{3-6}$cycloalkyl, $C_{1-6}$alkoxy, $C_{1-4}$alkylthio and $C_{3-6}$cycloalkoxy, said $C_{1-6}$alkyl, $C_{3-6}$cycloalkyl, $C_{1-6}$alkoxy, $C_{1-4}$alkylthio and $C_{3-6}$cycloalkoxy optionally substituted from one up to the maximum number of substitutable positions with halo, C is phenyl or C is not present;

when C is not present then B is selected from the group consisting of: $C_{5-16}$alkyl, $C_{5-16}$alkenyl, $C_{5-16}$alkynyl, and $C_{4-15}$alkoxy, and when C is phenyl then B is $C_{1-6}$alkyl.

2. The compound according to claim 1 wherein:
Ar is phenyl and
the group —B—C is attached to the phenyl ring at the 3- or 4-position.

3. The compound according to claim 1 wherein X is a bond, m is 2 and n is 2.

4. The compound according to claim 1 wherein X is selected from O, NH or S, m is 1 and n is 2.

5. The compound according to claim 1 wherein C is not present and B is selected from the group consisting of: $C_{5-16}$alkyl, $C_{5-16}$alkenyl, $C_{5-16}$alkynyl, and $C_{4-15}$alkoxy.

6. The compound according to claim 1 wherein C is phenyl and B is $C_{1-6}$alkyl.

7. The compound according to claim 1 wherein:
B—C is selected from the group consisting of:
(1) B is $C_{7-10}$alkyl and C is not present,
(2) B is $C_{6-9}$alkoxy and C is not present, or
(3) B is $C_{1-6}$alkyl and C is phenyl.

8. The compound in accordance with claim 1 wherein:
when X is a bond then m is 2 and n is 2,
when X is O, NH or S then m is 1 and n is 2,
the group —B—C is attached to the phenyl ring at the 3- or 4-position.

9. The compound in accordance with claim 8 wherein C is not present and B is selected from the group consisting of: $C_{5-16}$alkyl, $C_{5-16}$alkenyl, $C_{5-16}$alkynyl, and $C_{4-15}$alkoxy.

10. The compound in accordance with claim 9 wherein C is not present and B is $C_{7-10}$alkyl.

11. The compound in accordance with claim 9 wherein C is not present and B is $C_{6-9}$alkoxy.

12. The compound in accordance with claim 8 wherein C is phenyl and B is $C_{3-6}$alkyl.

13. The compound in accordance with claim 8 wherein A is selected from the group consisting of: —$CO_2H$, —$PO_3H_2$, —$PO_2H_2$, —$SO_3H$ and —$PO(R^8)OH$.

14. A compound selected from the group consisting of:

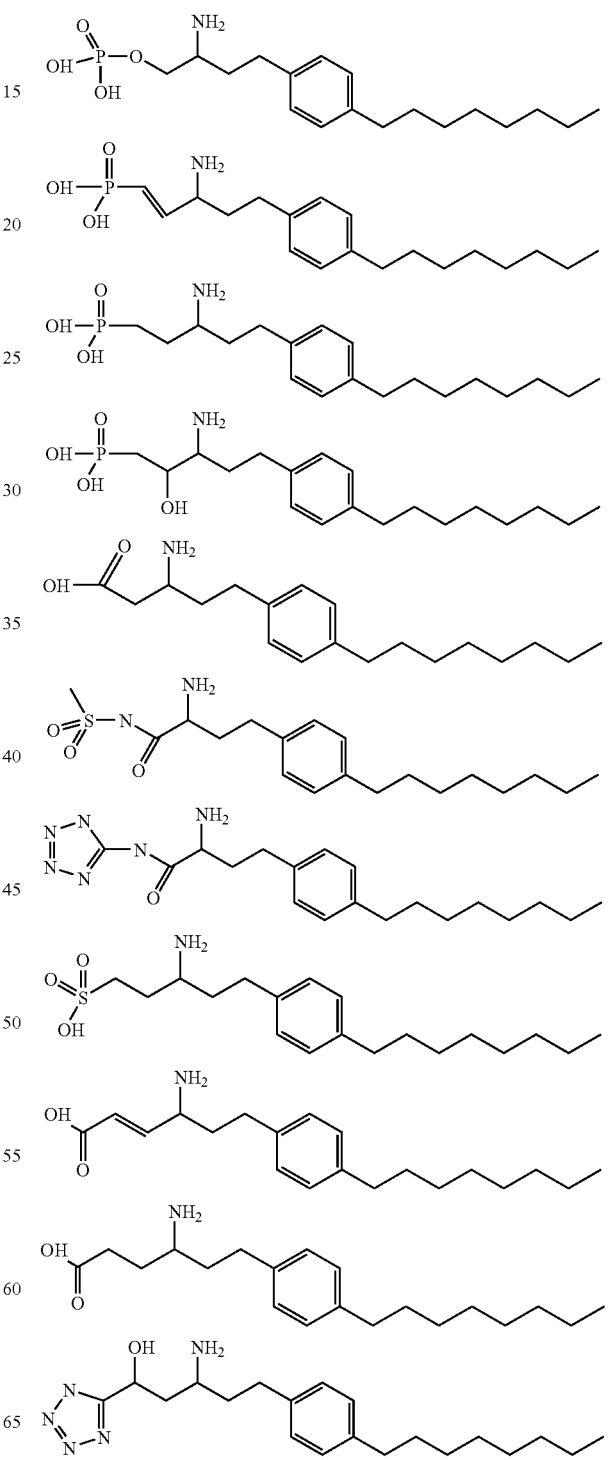

-continued
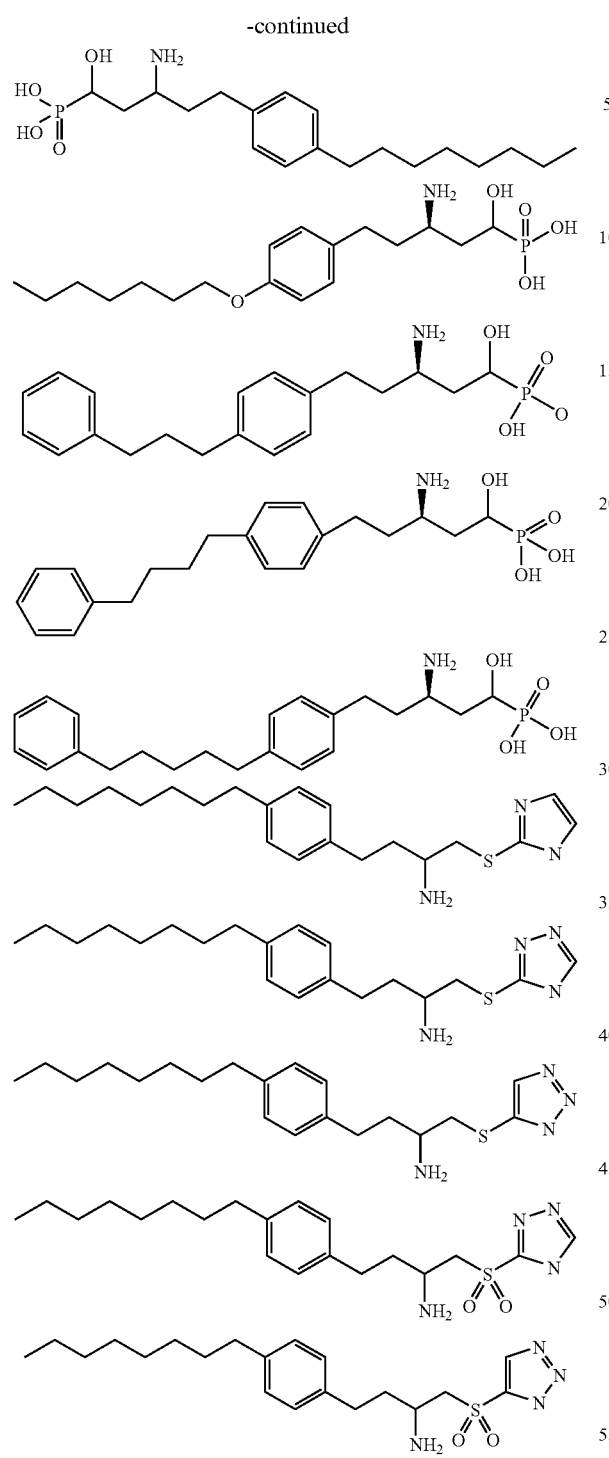
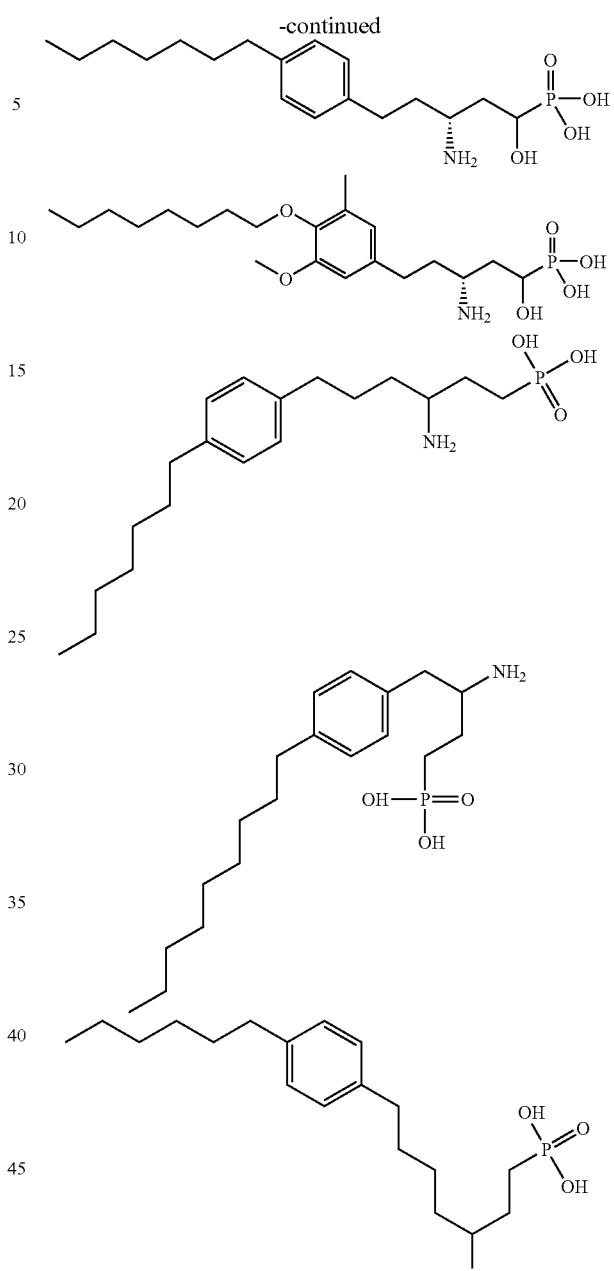
or a pharmaceutically acceptable salt of any of the above.
15. A pharmaceutical composition comprised of a compound in accordance with claim 1 in combination with a pharmaceutically acceptable carrier.
* * * * *